United States Patent [19]

Yu et al.

[11] Patent Number: 5,462,940
[45] Date of Patent: Oct. 31, 1995

[54] 4-OXOCYCLIC UREAS USEFUL AS ANTIARRHYTHMIC AND ANTIFIBRILLATORY AGENTS

[75] Inventors: Chia-Nien Yu; Stanford S. Pelosi, Jr., both of Norwich; Mark A. Calcagno, Oxford, all of N.Y.

[73] Assignee: Norwich Eaton Pharmaceuticals, Inc., Norwich, N.Y.

[21] Appl. No.: 275,461

[22] Filed: Jun. 3, 1994

Related U.S. Application Data

[63] Continuation of Ser. No. 59,862, May 10, 1993, abandoned, which is a continuation of Ser. No. 744,867, Aug. 14, 1991, abandoned.

[51] Int. Cl.$^6$ .................. A61K 31/535; A61K 31/495; A61K 31/55; C07D 413/00; C07D 403/00; C07D 401/00; C07D 421/00; C07D 241/02

[52] U.S. Cl. .................. 514/235.8; 514/212; 514/252; 514/253; 514/326; 540/597; 540/601; 544/139; 544/295; 544/357; 544/360; 544/363; 544/370; 546/210

[58] Field of Search .................. 544/139, 370, 544/360, 357, 295, 363; 546/210; 540/597, 601; 514/212, 252, 253, 235.8, 326

[56] References Cited

U.S. PATENT DOCUMENTS

| | | | |
|---|---|---|---|
| 3,415,821 | 12/1968 | Davis et al. | 260/240 |
| 4,393,204 | 7/1983 | Pelosi, Jr. | 542/420 |
| 4,543,359 | 9/1985 | Ellis et al. | 514/390 |
| 4,689,341 | 8/1987 | Diamond et al. | 514/399 |
| 4,705,799 | 11/1987 | Gregory | 514/376 |
| 4,707,499 | 11/1987 | Baran et al. | 514/471 |
| 4,713,382 | 12/1987 | Pascal | 514/255 |
| 4,720,580 | 1/1988 | Buzby et al. | 564/89 |
| 4,775,670 | 10/1988 | Sykes et al. | 514/210 |
| 4,804,662 | 2/1989 | Nickisch et al. | 544/370 |
| 4,806,536 | 2/1989 | Cross et al. | 544/370 |
| 4,851,526 | 7/1989 | Greenberg et al. | 544/370 |
| 4,870,095 | 9/1989 | Bailey | 514/466 |
| 4,876,262 | 10/1989 | Oinuma et al. | 514/318 |
| 4,963,561 | 10/1990 | Lesher et al. | 514/303 |
| 4,966,967 | 10/1990 | Lumma, Jr. et al. | 540/568 |
| 4,994,459 | 2/1991 | Butera et al. | 544/370 |

FOREIGN PATENT DOCUMENTS

| | | |
|---|---|---|
| 0235752 | 9/1987 | European Pat. Off. |
| 0347733 | 12/1989 | European Pat. Off. |
| 0431945 | 12/1991 | European Pat. Off. |

OTHER PUBLICATIONS

Bigger, J. T. and Hoffman, B. F., "Antiarrhythmic Drugs", Ch. 35 in Goodman and Gilman's The Basis of Pharmaceutical Therapeutics, 8th ed., ed., A. G. Gilman, pp. 840–873 (1990).
Bigger, J. T., "Antiarrhythmic Treatment: An Overview", American Journal of Cardiology, vol. 53, pp. 8B–16B, Feb. 27, 1984.
Woosley, R. L., "Antiarrhythmic Agents", in the Heart, Ch. 95, pp. 1682–1711, ed. J. W. Hurst, New York, McGraw-Hill (1990).
Woosley, R. L., "Antiarrhythmic Drugs", Annual Review, Pharmacology and Toxicology, vol. 31, pp. 427–455 (1991).
Morganroth, J. and Bigger, J. T., "Pharmacological Management of Ventricular Arrhythmias After the Cardiac Arrhythmia Suppression Trail", American Journal of Cardiology, vol. 65, pp. 1497–1503 (1990).
Goldstein, S., "Toward a New Understanding of the Mechanism and Prevention of Sudden Death in Coronary Heart Disease", Circulation, vol. 82(1):pp. 284–288 (1990).
Echt, D. S. et al. "Mortality and Morbidity in Patients Receiving Encainide, Flecainide, or Placebo: The Cardiac Arrhythmia Suppression Trail", New England Journal of Medicine, vol. 324, pp. 781–788 (1991).
Coplen, S. E. et al. "Efficacy and Safety of Quinidine Therapy for Maintenance of Sinus Rhythm After Cardioverison: A Meta-analysis" Circulation, vol. 82, pp. 1106–1116 (1990).

*Primary Examiner*—Cecilia Tsang
*Attorney, Agent, or Firm*—Karen F. Clark; David L. Suter; Jacobus C. Rasser

[57] ABSTRACT

The 4-oxocyclic ureas and the pharmaceutically acceptable salts and esters thereof, of the present invention are useful as antiarrhythmic and antifibrillatory agents and have the following general structure:

$$R_1 \underset{R_2}{\overset{X}{\diamond}} R_3 - R - \underset{}{\overset{Y}{\diamond}} - L - N \underset{(R_5)}{\diamond} \underset{O}{\overset{O}{\diamond}} N - R_{4A}$$

wherein X, Y, A, L, R, $R_1$, $R_2$, $R_3$, $R_4$ and $R_5$ are defined as in the specification.

35 Claims, No Drawings

4-OXOCYCLIC UREAS USEFUL AS ANTIARRHYTHMIC AND ANTIFIBRILLATORY AGENTS

This is a continuation of application Ser. No. 08/059,862, filed May 10, 1993, now abandoned, which is a continuation of application Ser. No. 07/744,867, filed on Aug. 14, 1991, abandoned.

BACKGROUND OF THE INVENTION

The present invention relates to novel 4-oxocyclic urea compounds and pharmaceutical compositions thereof, useful in treating humans or other mammals with cardiac arrhythmia and/or cardiac fibrillation.

The novel 4-oxocyclic urea compounds of the present invention are active as antifibrillatory and antiarrhythmic agents. The present compounds exhibit broad efficacy against cardiac arrhythmia and fibrillation and can be satisfactorily applied to substantially alleviate and/or prevent arrhythmia and fibrillation. In addition, said compounds exhibit a lower incidence of some of the undesirable side effects than do many conventional antiarrhythmic therapies. An additional benefit of the compounds described herein is that they exhibit both antifibrillatory and antiarrhythmic activity; most conventional therapies generally do not exhibit efficacy as antifibrillatory agents. See, e.g., Coplen, S. E. et al., "Efficacy and Safety of Quinodine Therapy for Maintenance of Sinus Rhythm After Cardioversion:A meta-analysis," *Circulation*, Vol 82, pp. 1106–1116 (1990); Echt, D. S. et al., "Mortality and Morbidity in Patients Receiving Ecainide, Flecainide, or Placebo. The Cardiac Arrhythmia Suppression Trial", *New England Journal of Medicine*, Vol. 324, pp. 781–788 (1991), both hereby incorporated by reference herein.

In a healthy, structurally sound heart, the precise, sequential electrical activation, then deactivation, of the entire cardiac muscle that occurs unerringly with each beat is characterized as normal cardiac rhythm. Arrhythmias are characterized as occurrences of abnormal electrical activity that can interfere with normal cardiac rhythm. The abnormal electrical activity can interfere with the initiation of, and/or the uniform spread of, the electrical wave (i.e. depolarization followed by repolarization of the cardiac muscle) that triggers the heart to contract. The disruption of the smooth, cyclical process of cardiac function associated with normal cardiac rhythm by the existence of arrhythmias is, in some instances, life-threatening.

Arrhythmias range in severity from relatively benign (consisting of asymptomatic and infrequent premature ventricular complexes [PVCs]) to life-threatening (consisting of ventricular fibrillation, and sustained ventricular tachyarrhythmia). For an excellent review of arrhythmias and an overview of antiarrhythmic therapy, see, e.g. Bigger, Thomas J., "Antiarrhythmic Treatment: An Overview", *American Journal of Cardiology*, Vol. 53, pp. 8B-16B, Feb. 27, 1984; Goldstein, S. "Toward A New Understanding of the Mechanism and Prevention of Sudden Death in Coronary Heart Disease," *Circulation*, Vol. 87(1), pp. 284–88 (1990); and Woolsey, R. L., "Antiarrhythmic Drugs", *Annual Review Pharmacology and Toxicology*, Vol. 31:pp. 427–455 (1991), all hereby incorporated by reference herein.

Life-threatening arrhythmias are noted as a leading cause of death worldwide. For instance, it is estimated that sudden cardiac death resulting from ventricular fibrillation kills approximately 400,000–600,000 people in the United States each year. See U.S. Department of Health and Human Services (1985) NCHS Monthly Vital Statistics Report 33:8–9.

Arrhythmias are generally classified into two types: 1) Supraventricular Arrhythmias (for example, atrial fibrillation and flutter) and 2) Ventricular Arrhythmias (for example, ventricular tachyarrhythmia and ventricular fibrillation and flutter).

Supraventricular arrhythmias are generally not life threatening. Individuals with these arrhythmias may experience a wide range of symptoms, from slight to severe intensity. These individuals may feel the physical sensation of missed beats, extra beats, and/or flutter, may occasionally feel slightly light-headed or dizzy, and may have shortness of breath and/or chest pain. Since this situation is, in fact, generally not life threatening, more aggressive therapies such as conventional antiarrhythmic drugs are sometimes not prescribed, because the side effects usually associated therewith may not be acceptable for a non-life-threatening condition. However, the novel compounds of the present invention are generally much better tolerated than many of the conventional, currently available antiarrhythmics and, therefore, they would be an acceptable therapy for individuals suffering from supraventricular arrhythmias and would substantially alleviate the discomfort these individuals experience.

Ventricular arrhythmias, on the other hand, are potentially much more serious and have been classified into three groups: 1) benign; 2) prognostically-significant (potentially lethal); and 3) life threatening (lethal). See, e.g. Morganroth, J. and Bigger, J. T., "Pharmacological Management of Ventricular Arrhythmias After the Cardiac Arrhythmia Suppression Trial", *American Journal of Cardiology*, Vol. 65, pp. 1497–1503, 1990, hereby incorporated by reference herein, (hereinafter *Morganroth and Bigger*).

Individuals with benign arrhythmias exhibit very low risk of death, cardiac scarring, and heart disease. Benign ventricular arrhythmias are relatively common and account for approximately 30% of all ventricular arrhythmias. Id. Benign arrhythmias, such as premature ventricular complexes (PVCs), pose minimal risks to individuals and rarely require antiarrhythmic therapy. However, the PVCs may be of a frequency or complexity, or are associated with sufficiently alarming symptoms, so that individuals experiencing them do not respond to reassurance that the arrhythmias and symptoms are not dangerous. They also may not respond to more conventional treatment (e.g., beta-blockers). In these cases, treatment with the novel compounds of the present invention will likely be beneficial in these individuals.

Prognostically significant arrhythmias are usually associated with some other clinical presentation of cardiac disease, such as mild heart failure, ischemic symptoms, and/or cardiac scarring. It has been stated that approximately 65% of all ventricular arrhythmias are prognostically significant. See, e.g. *Morganroth and Bigger*, at 1497.

Patients with life threatening arrhythmias may present with syncope (sudden loss of consciousness—usually fainting— associated with insufficient brain perfusion), cardiac arrest, heart failure, and/or myocaridal ischemia, in the presence of structural heart disease. Life threatening arrhythmias are relatively uncommon; probably less than 10% of the individuals suffering from arrhythmias suffer from a life threatening form. See *Morganroth and Bigger* at 1497. However, due to the life-threatening nature of lethal ventricular arrhythmias, and the severity of the symptoms associated therewith, they must be aggressively treated.

The novel compounds of the present invention are efficacious against cardiac fibrillation and supraventricular and ventricular arrhythmias. In addition, the novel compounds of the present invention generally exhibit less of some of the undesirable effects which have come to be tolerated in many of the traditional antiarrhythmic drugs, for lack of acceptable alternate therapies. For example, many current therapies cause pulmonary toxicity, cardiac depression, and neurologic effects not specific to cardiac tissue. For an excellent discussion of the side effects associated with conventional antiarrhythmic therapies see, e.g., Bigger, J. T. and Hoffman, B. F., "Antiarrhythmic Drugs" in *Goodman and Gilman's The Basis of Pharmacological Therapeutics*, 8th edition, ed. A. G. Gilman, pp. 840–873, New York: Pergamon; and Woolsey, R. L. "Antiarrhythmic Agents," in *The Heart*, ed. J. W. Hurst, pp. 1682–1711, New York, McGraw-Hill (1990), both hereby incorporated by reference herein.

In addition, the novel compounds of the present invention are readily bioavailable. This facilitates treatment by oral administration, and therefore greatly facilitates patient compliance. In addition, the novel compounds of the present invention are relatively inexpensive to manufacture, and they exhibit a high degree of stability in oral dosage forms.

SUMMARY OF THE INVENTION

The novel 4-oxocyclic ureas of the present invention, and the pharmaceutically-acceptable salts and esters thereof, are useful as antiarrhythmic and antifibrillatory agents and have the following general structure:

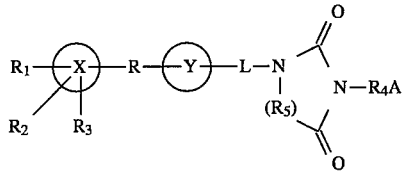

wherein (a) X is a saturated or unsaturated, 5-, 6-, or 7-membered heterocycle or carbocycle;

(b) R is selected from the group consisting of covalent bond, nil, heteroatom, carbonyl, heterocyclic ring, carbocyclic ring, alkyl, alkenyl, alkoxy, alkylamino, arylalkyl, aryloxy, acyl, acyloxy, and acylamino;

(c) Y is a substituted or unsubstituted, saturated or unsaturated, 5-, 6-, or 7-membered heterocyclic ring or carbocyclic ring, or is nil;

and wherein when R is nil, X and Y are fused ring systems; and when R is a covalent bond, X and Y are ring systems linked through a covalent bond; and when Y is nil, R is a covalent bond, and X is bound to L through R;

(d) $R_1$, $R_2$, and $R_3$ are independently selected from the group consisting of nil, Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino and acyloxy;

(e) L is selected from the group consisting of alkylamino, alkenylamino, alkyl imino, alkenyl imino, and acylamino; wherein the nitrogen atom thereof is bound to the nitrogen atom at the 1-position of the 4-oxocyclic urea moiety;

(f) $R_4$ is selected from the group consisting of alkyl, alkenyl, alkynyl, alkylacyl, and heteroalkyl;

(g) A is a substituted or unsubstituted, saturated or unsaturated, straight-chain or branched, a 3–8 member heteroalkyl comprising 1–7 carbon atoms or a substituted or unsubstituted, saturated or unsaturated heterocycle having 5-, 6-, or 7-members; and A has one nitrogen atom, which is adjacent to $R_4$; and (h) $R_5$ is a substituted or unsubstituted $C_1$ or $C_2$ alkyl.

THE RING SYSTEM (X-R-Y).

The novel 4-oxocyclic urea compounds of the present invention are comprised of a 4-oxocyclic urea moiety connected to a ring system (X-R-Y) via a linking moiety (L). The 4-oxocyclic ureas have a nitrogen atom at the 3-position which is substituted with an amino-containing moiety (A) consisting of an amino group separated from the nitrogen at the 3-position of the 4-oxocyclic urea moiety by a spacing group ($R_4$). The moiety represented by (X-R-Y) is a ring system moiety and consists of one or more, preferably one or two, fused or unfused, saturated or unsaturated, substituted or unsubstituted, carbocyclic rings or heterocyclic rings as defined herein. Each carbocyclic ring or heterocyclic ring contains 5, 6, or 7, preferably 5 or 6, members.

It is preferable that the ring system (X-R-Y) is polycyclic and is comprised of two, unfused rings and even more preferable that the ring represented by Y which is adjacent to the linking moiety, L, be a heterocycle, most preferably a five-membered ring which contains an oxygen heteroatom at the 1-position. In addition, when there are two rings in the ring system, it is also preferable that the heterocycle (Y) is covalently bound to the other ring (X) at the 5-position of the heterocycle and at the 1-position of X, and that the heterocycle Y is bound to the L moiety at the 2-position of Y.

Although not preferred, it is also possible for the ring system (X-R-Y) to consist of two rings (X and Y) which are separated by an alkyl, carbonyl, or a heteroatom, most preferably oxygen (R). In addition, the ring system may be monocyclic; in this case, Y is nil and R is a covalent bond attached to L. However, when there is only one ring in the system, it is preferable that said ring be substituted with at least two, and most preferably at least three, substituents chosen from the group consisting of, but not limited to, hydroxy, methyl, Cl, methoxy, and benzoyl.

When substituted, any or all of the members of the ring system (whether monocyclic or polycyclic) may have one or more substituents, and may be substituted with Cl, F, Br, $NH_2$, $CF_3$, OH, $SO_3H$, $CH_3SO_2NH$, COOH, alkoxy, alkyl, alkoxycarbonyl, carboxyalkyl, aminoalkyl, acylamino or acyloxy;

THE LINKING MOIETY (L)

L is the linking moiety of the novel 4-oxocyclic urea compounds of the present invention. The carbon-containing end of L is bound on to the ring system at Y, but if Y is nil, at X; most preferably at the 2-position of the Y ring or at the 1-position of the X, if Y is nil. The nitrogen atom of the L moiety is bound to the nitrogen atom at the 1-position of the 4-oxocyclic urea moiety. The L moiety is selected from the group consisting of, but not limited to, alkylamino, alkenylamino, alkylimino, alkenylimino, and acylamino; L is preferably an alkylimino, most preferably a $C_1$ alkylimino, CH=N.

THE 4-OXOCYCLIC UREA MOIETY

The 4-oxocyclic urea moiety of the novel compounds of the present invention gives the novel compounds of the present invention their characteristic name. The 4-oxocyclic urea moiety may be a 5- or 6-membered ring, preferably a 5-membered ring. The 4-oxocyclic urea moiety is connected to the nitrogen atom of the linking moiety (L) at the nitrogen atom at the 1-position of the 4-oxocyclic urea moiety. The 4-oxocyclic urea moiety has the following structure:

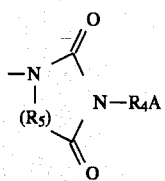

wherein $R_5$ is a $C_1$ or $C_2$ alkyl, preferably a $C_1$ alkyl. A is a heteroalkyl or a heterocyclic ring, and must always contain at least one nitrogen atom, which is attached to $R_4$. When A is a heteroalkyl, A may be straight-chained or branched, saturated or unsaturated, substituted or unsubstituted. When A is a heterocycle, A is a 5-, 6-, or 7 -membered heterocyclic ring. Said ring may be substituted or unsubstituted, preferably substituted, and saturated or unsaturated, preferably saturated. $R_4$ is connected to the nitrogen atom at the 3-position of the 4-oxocyclic urea moiety and to a nitrogen atom of A. $R_4$ is selected from the group consisting of, but not limited to alkyl, alkenyl, alkynyl, alkyl acyl, and heteroalkyl.

When A is a substituted heteroalkyl, the substituents are selected from the group consisting of, but not limited to, methyl, hydroxyethyl, alkyl, aryl, heterocycle, aryl alkyl, mercaptoethyl, and methanesulfonyl.

When heterocycle A has two heteroatoms and both are nitrogen, it is preferable that the nitrogen atom not adjacent to $R_4$ be substituted with substituents selected from the group consisting of, but not limited to, methyl, hydroxyethyl, alkyl, aryl, heterocycle, arylalkyl, mercaptoethyl, and methanesulfonyl. When heterocycle A has only 1 nitrogen atom, it is preferable that the heterocycle A be substituted (at the position para to the nitrogen connected to $R_4$ if the heterocycle A has 6-members) with substituents selected from the group consisting of, but not limited to, hydroxyethyl, hydroxy, oxo and methyl.

DEFINITIONS AND USAGE OF TERMS

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated hydrocarbon chain having 1 to 8 carbon atoms, and preferably, unless otherwise stated, from 1 to 4 carbon atoms. Preferred alkyl groups include, but are not limited to, methyl, ethyl, propyl, isopropyl, and butyl.

"Heteroalkyl" is an unsubstituted or substituted, saturated chain having from 3 to 8-members and comprising carbon atoms and one or two heteroatoms.

"Alkenyl" is an unsubstituted or substituted, straight-chain or branched, hydrocarbon chain having from 2 to 8 carbon atoms, preferably from 2 to 4 carbon atoms, and having at least one olefinic double bond.

"Alkynyl" is an unsubstituted or substituted, straight-chain or branched, hydrocarbon chain having from 2 to 8 carbon atoms, preferably from 2 to 4 carbon atoms, and having at least one triple bond.

"Ring System" as used herein refers to the ring-containing moiety to which the 4-oxocyclic urea moiety is connected through the linking moiety, L. It is denoted herein by "X-R-Y" and may be a monocyclic ring moiety, or a fused, bridged, or spiro polycyclic ring moiety, and may contain carbocycles, heterocycles, or both. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms.

"Heterocyclic ring" or "Heterocycle" as used herein is an unsubstituted or substituted, saturated, unsaturated or aromatic ring comprised of carbon atoms and one or more heteroatoms in the ring. Heterocyclic rings generally contain from 3 to 8, preferably 5 to 7, atoms. Unless otherwise stated the heteroatoms may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O—alkyl or —O—alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl, hydroxypropyl, phenylhydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., NH—alkyl-) such as dimethylamino alkyl.

"Alkylamino" is an amino moiety having one or two alkyl substituents (e.g., —N-alkyl).

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl-).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a moiety formed by removal of the hydroxy from a carboxylic acid (e.g., R—C(=O)—). Preferred alkylacyl groups include, but are not limited to, acetyl, propionyl, and butanoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halides (such as chloride) salts.

A "biohydrolyzable ester" is an ester of the 4-oxocyclic urea compounds that does not interfere with the antiarrhythmic activity of the compounds, or that is readily metabolized by a human or other mammal to yield an antiarrhythmically-active 4-oxocyclic urea. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxymethyl, acetoxyethyl, aminocarbonyl oxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl oxymethyl, ethoxycarbonyl oxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE PRESENT INVENTION

The present invention encompasses certain novel 4-oxocyclic ureas, methods for their manufacture, pharmaceutical compositions thereof, and a method of treatment utilizing said novel compounds and compositions thereof for treating cardiac arrhythmias and/or cardiac fibrillation in humans or other mammals. Specific compounds and compositions to be used in the invention must, accordingly, be pharmaceutically-acceptable. As used herein, such a "pharmaceutically-acceptable" component is one that is suitable for use with humans and/or other mammals without undue adverse side effects (such as toxicity, irritation, and allergic response), commensurate with a reasonable benefit/risk ratio.

Novel 4-Oxocyclic Urea Compounds

The compounds of this invention, herein referred to as "4-oxocyclic ureas", encompass any of a variety of 4-oxocyclic urea compounds having the general structure:

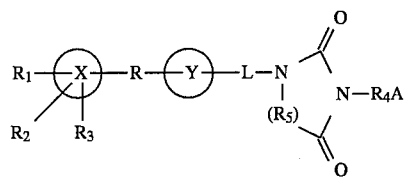

wherein
(a) X is a saturated or unsaturated, 5-, 6-, or 7-membered heterocycle or carbocycle;
(b) R is selected from the group consisting of covalent bond, nil, heteroatom, carboxyl, heterocyclic ring, carbocyclic ring, alkyl, alkenyl, alkoxy, alkylamino, arylalkyl, aryloxy, acyl, acyloxy, and acylamino;
(c) Y is a substituted or unsubstituted, saturated or unsaturated, 5-, 6-, or 7-membered heterocycle or carbocycle; or is nil;
and wherein when R is nil, X and Y are fused ring systems; and when R is a covalent bond, X and Y are ring systems linked through a covalent bond; and when Y is nil, R is a covalent bond and X is bound to L through R;
(d) $R_1$, $R_2$, and $R_3$ are independently selected from the group consisting of nil, Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino, and acyloxy;
(e) L is selected from the group consisting of alkylamino, alkenylamino, alkylimino, alkenylimino and acylamino; wherein the nitrogen atom of L is bound to the nitrogen atom at the 1-position of the 4-oxocyclic urea moiety;
(f) $R_4$ is selected from the group consisting of alkyl, alkenyl, alkynyl, alkylacyl and heteroalkyl;
(g) A is a substituted or unsubstituted, saturated or unsaturated, straight-chain or branched a 3–8 member heteroalkyl comprising 1–7 carbon atoms or a substituted or unsubstituted, saturated or unsaturated heterocycle having 5-, 6-, or 7-members; and A has at least one nitrogen atom which is adjacent to $R_4$, and
(h) $R_5$ is a substituted or unsubstituted $C_1$ or $C_2$ alkyl;
and the pharmaceutically-acceptable salts and esters thereof.

THE RING SYSTEM (X-R-Y)

The novel 4-oxocyclic urea compounds of the present invention are comprised of a 4-oxocyclic urea moiety connected to a ring system (X-R-Y) via a linking moiety (L). The 4-oxocyclic ureas have a nitrogen atom at the 1-position and also at the 3-position. The nitrogen atom at the 3-position is substituted with an amino-containing group (A) separated from the nitrogen atom at the 3-position by a spacing group ($R_4$).

The ring system (X-R-Y) is a ring-containing moiety and consists of one or more, preferably one or two, fused or unfused, saturated or unsaturated, substituted or unsubstituted, rings as defined herein. Accordingly, the ring system may be monocyclic (Y is nil) or polycyclic (both X and Y are rings or all of X, R, and Y are rings). Each ring may be either a carbocycle or a heterocycle, and may contain 5, 6, or 7, preferably 5 or 6, members.

It is preferable that the ring system is polycyclic and is comprised of two, unfused rings. It is more preferable that the ring (Y) adjacent to the linking moiety (L) is a heterocycle, most preferably a five-membered ring which contains an oxygen atom at the 1-position. In addition, when there are two rings in the ring system, it is preferable that the heterocycle (Y) is covalently bound (through R) to the other ring (X) at the 5-position of the heterocycle Y and at the 1-position of ring X, and that heterocycle Y is bound to the carbon-containing end of the L moiety at the 2-position of the heterocycle.

Although not preferred, it is acceptable for the ring system to be a polycyclic ring system comprised of two rings (X and Y) which are separated by an alkyl, a carbonyl, or a heteroatom, preferably oxygen (R). In addition, a suitable ring system might include a polycyclic ring system comprised of two rings (X and Y) which are fused (R is nil) or three rings (X, R, and Y), which are fused. When R is a ring, it is preferably a 5- or 6-membered carbocycle or heterocycle.

A particularly suitable ring system is monocyclic, therefore, consisting of only one ring (X) which is covalently bound to the carbon-containing portion of L (R is a covalent bond and Y is nil). However, when there is only one ring in the ring system, it is preferable that the ring be a 6-membered carbocycle, which is more preferably substituted with at least two, and most preferably with at least three, substituents independently chosen from the group consisting of, but not limited to, hydroxy, methyl, chloro, methoxy, and benzoyl.

When substituted, any or all of the members of the ring system, whether monocyclic or polycyclic, may have one or more substituents. Said substituents may be independently selected from the group consisting of, and not limited to, Cl, F, Br, $NH_2$, $CF_3$, OH, $SO_3H$, $CH_3SO_2NH$, COOH, alkoxyl, alkoxycarbonyl, hydroxyalkyl, alkyl, aminoalkyl, acylamino, acyloxy and carboxyalkyl, especially Cl, F, Br, OH, and $CH_3$.

Preferred ring systems of the novel 4-oxocyclic ureas include, but are not limited, for example, to monocyclic rings including, but not limited to, 2-acetoxy-5-chlorophenyl; 3-hydroxy-5-hydroxymethyl-2-methyl-4-pyridinyl; 2-thienyl; 4-pyrimidinyl; 5-methoxycarbonyl-2-furanyl; cyclohexyl; 5-chloro-2-hydroxyphenyl; 5-chloro-2-methoxyphenyl; 2-methanesulfonyl aminophenyl; 3-aminophenyl; 2-methoxyphenyl; 5-ethyl-2-furanyl; 3-methoxyphenyl; 2-aminophenyl; 2-furanyl; 3,5-dimethyl-4-hydroxyphenyl; and 5-acetyloxymethyl-2-furanyl. Suitable polycyclic ring systems which consist of two unfused rings, covalently bound to one another include, for example, but are not limited to, 5-(4-carboxyphenyl)-2-furanyl; 5-(4-methanesulfonylphenyl)-2-furanyl; 5-(3,4-dimethoxyphenyl)-2-furanyl; 5-(4-methanesulfonylaminophenyl)-2-furanyl; 5-(4-bromophenyl)-2-oxazolyl; 5-(4-methoxyphenyl)-2-furanyl; 5-(1-cyclohexen-1-yl)-2-furanyl; 5-cyclohexyl-2-furanyl; 5-(3-trifluoromethylphenyl)-2-furanyl; 5-(4-methylphenyl)-2-furanyl; 2-(4-chlorophenyl)-3-furanyl; 5-(4-chlorophenyl)-2-furanyl; 5-(4-fluorophenyl)-2-furanyl. Suitable polycyclic ring systems which consists of two unfused rings each connected to one another via a heteroatom, alkyl, or other non-cyclic carbon-containing group include, for example, but are not limited to, 2-benzyloxy-5-chlorophenyl; 4-benzyloxyphenyl; 3-(4-t-butylphenyloxy)phenyl; 3-benzoyl-2,4-dichlorophenyl; 2-chloro-3-benzyloxyphenyl; 3-(4-chlorophenoxyl)phenyl. Suitable polycyclic ring systems containing two or more fused rings include, for example, but are not limited to, 1H-indol-3-yl; 2-fluorenyl; 2-naphthyl; 2-hydroxy-1-naphthyl; 2-quinolinyl; 5-chloro-2-benzofuranyl.

Preferred ring systems (X-R-Y) of the novel 4-oxocyclic ureas defined herein include, but are not limited to:

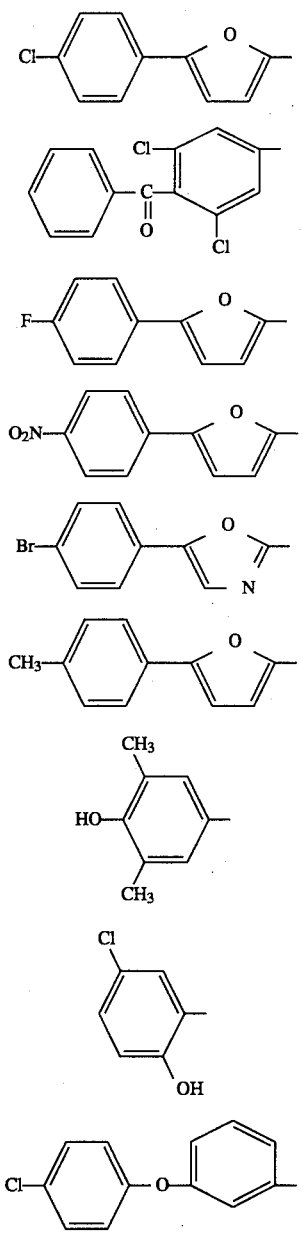

THE LINKING MOIETY (L)

L is the linking moiety of the novel 4-oxocyclic urea compounds of the present invention. The carbon-containing end of L is bound to the X-R-Y ring system at Y, but if Y is nil, at X; most preferably at the 2-position of the Y ring or at the 1-position of X, if Y is nil. The nitrogen atom of the L moiety is bound to the nitrogen atom at the 1-position of the 4-oxocyclic urea moiety. The L moiety is selected from the group consisting of alkylamino, alkenylamino, alkylimino, alkenylimino, and acylamino, preferably alkylimino, most preferably a $C_1$ alkylimino, CH=N.

THE 4-OXOCYCLIC UREA MOIETY

The 4-oxocyclic urea moiety of the novel compounds of the present invention gives the novel compounds of the present invention their characteristic name. The 4-oxocyclic urea moiety may be a 5- or 6-membered ring, preferably a 5-membered ring. The 4-oxocyclic urea moiety has the following structure:

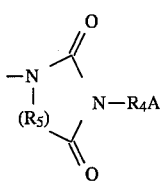

wherein $R_5$ is a $C_1$ or $C_2$ alkyl, preferably a $C_1$ alkyl. When $R_5$ is a $C_1$ alkyl, the 4-oxocyclic urea is a 5-membered ring and when $R_5$ is a $C_2$ alkyl, the 4-oxocyclic urea is a 6-membered ring.

A is a straight chain or branched, substituted or unsubstituted, saturated or unsaturated a 3–8 member heteroalkyl comprising 1–7 carbon atoms or a substituted or unsubstituted, saturated or unsaturated 5-, 6-, or 7-, preferably 5- or 6-, membered heterocyclic ring. The A moiety, whether a heteroalkyl or a heterocycle, must have at least one nitrogen atom, which must be bound to $R_4$.

When A is a substituted heteroalkyl, it is preferable that the substituents are selected from the group consisting of, but not limited to, methyl, hydroxyethyl, alkyl, aryl, heterocycle, arylalkyl, mercaptoethyl, and methanesulfonyl.

When A has two nitrogen atoms, it is preferable that the nitrogen atom not adjacent to $R_4$ (which in the case of a 6-membered heterocycle is para to the nitrogen atom adjacent to $R_4$) is substituted with substituents selected from the group consisting of, but not limited to, methyl, hydroxyethyl, alkyl, aryl, mercaptoethyl, methanesulfonyl, heterocycle and aryl alkyl. When heterocycle A has only one nitrogen atom, and A is a 6-membered ring, the position para to the nitrogen atom which is adjacent to $R_4$ is preferably substituted with substituents selected from the group consisting of, but not limited to, hydroxyethyl, hydroxy, oxo, and methyl.

Preferred amine-containing (A) moieties of the novel 4-oxocyclic ureas defined herein include, but are not limited to:

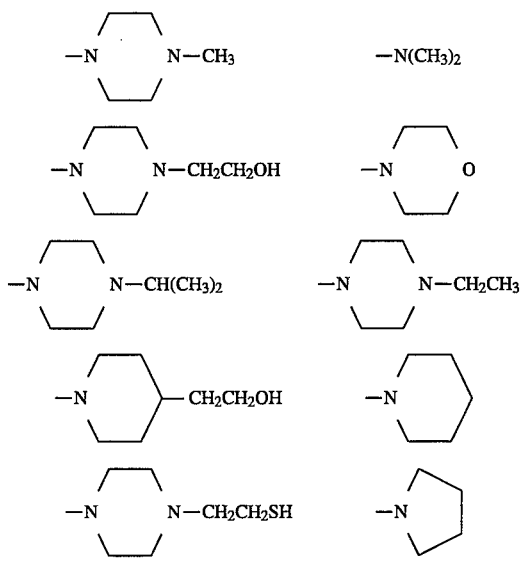

Suitable A moieties, accordingly, may include, but are not limited to, the following: Moieties where A is a heteroalkyl, include, but are not limited to, dimethylamino; diethylamino; bis-2-hydroxyethylamino; bis-[(1-methyl)ethyl]amino; N-benzyl-N-methylamino; N-(2-hydroxyethyl)-N-methylamino. Suitable A moieties where A is a heterocycle include, but are not limited to N-(1-methylethyl)-N-[2-hydroxy-2-[(4-methanesulfonylamino)phenyl] ethyl]amino, 4-phenylpiperazinyl; 4-(2-hydroxyethyl)piperazinyl; 4-(1-methylethyl)piperazinyl; 4-(2-methylpropyl)piperazinyl; 4-hexylpiperazinyl; 4-benzylpiperazinyl; 1-piperazinyl; 4-hydroxy-1-piperidinyl; 4-methyl-1-piperazinyl; 4-n-butyl-1-piperazinyl; 4-ethyl-1-piperazinyl; 3-(4-methyl-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; N-methyl-N-phenylamino; 1-imidazolyl; 4-(2-methylphenyl)-1-piperazinyl; 4-(4-methanesulfonylaminophenyl)-1-piperazinyl; N-morpholinyl; N-thiomorpholinyl; 4-oxo-1-piperidinyl; 2-(t-butoxycarbonyl)-1-pyrrolidinyl; pyrrolidinyl; 4-(4-acetylphenyl)-1-piperazinyl; hexahydro-1H-azepin-1-yl.

$R_4$ is connected to the nitrogen atom at the 3-position of the 4-oxocyclic urea moiety and to a nitrogen atom of A. $R_4$ is selected from the group consisting of, and not limited to alkyl, alkenyl, alkynyl, alkylacyl, and heteroalkyl, especially $C_3$–$C_6$ alkyl, i.e. propyl, butyl, pentyl, and hexyl.

As stated hereinabove, the novel 4-oxocyclic urea compounds of the present invention are comprised of a 4-oxocyclic urea moiety connected to a ring system via a linking moiety. Accordingly, suitable compounds of the present invention include, but are not limited to, the following compounds, and the pharmaceutically-acceptable esters and salts thereof, especially the hydrochloride salts thereof: 1-[[[5-(4-chlorophenyl)-2-furanyl]methylene]amino]-3 -[4-(4-methyl-1-piperazinyl)butyl]-2,4-imidazolidinedione; 1-[[[4-hydroxy-3,5-dimethylphenyl]methylene]amino]-3-[4-(4-methyl-1-piperazinyl)butyl]-2,4-imidazolidinedione; 1-[[[5-(4-chlorophenyl)-2-furanyl]methylene]amino]-3-[3-[4-(1-methylethyl)-1-piperazinyl]propyl]-2,4-imidazolidinedione; 1-[[[5-(4-chlorophenyl)-2-furanyl]methylene]amino]-3-[3-[4-(2-hydroxyethyl)-1-piperazinyl]propyl]-2,4-imidazolidinedione; 1-[[[5-(4-chlorophenyl)-2-furanyl]methylene]amino]-3-[6-(4-methyl-1-piperazinyl)hexyl]-2,4-imidazolidinedione; 1-[[[5-(4-chlorophenyl)-2-furanyl]methylene]amino]-3-[5-(4-methyl-1-piperazinyl)pentyl]-2,4-imidazolidinedione; 1-[[[5-(4-fluorophenyl)-2-furanyl]methylene]amino]-3-[4-(4-methyl-1-piperazinyl)butyl]-2,4-imidazolidinedione; 1-[[[5-(4-chlorophenyl)-2-furanyl]methylene]amino]-3-[4-[4-(2-hydroxyethyl)-1-piperidinyl]butyl]-2,4-imidazolidinedione; 1-[[[5-(4-chlorophenyl)-2-furanyl]methylene]-3-[3-[4-(2-hydroxyethyl)-1-piperidinyl]propyl]-2,4-imidazolidinedione; 1-[[[5-[4-chlorophenyl)-2-furanyl]methylene]amino]-3-[3-[4-(2-mercaptoethyl)-1-piperazinyl]propyl]-2,4-imidazolidinedione; 1-[[[5-(4-bromophenyl)-2-oxazolidinyl]methylene]amino]-3-[4-[4-methyl-1-piperazinyl)butyl]2,4-imidazolidinedione; 1-[[[5-(4-chlorophenyl)-2-furanyl]methylene]amino]-3-[3-(dimethylamino)propyl]dihydro-2,4-(1H,3H)pyrimidinedione; 1-[[[5-(4-chlorophenyl)-2-furanyl]methylene]amino]-3-(3-dimethylaminopropyl)-2,4-imidazolidinedione; 1-[[[5-(4-chlorophenyl)-2-furanyl]methylene]amino]-3-[3-(4-methyl-1-piperazinyl)propyl]-2,4-imidazolidinedione; 1-[[[5-(4-fluorophenyl)-2-furanyl]methylene]amino]-3-[3-[4-(2-hydroxyethyl-1-piperazinyl]propyl]-2,4-imidazolidinedione; 1-[[[5-(4-chlorophenyl)-2-furanyl]methylene]amino]-3-[ 8-(4-morpholinyl)octyl]-2,4-imidazolidinedione.

Examples A–L herein illustrate how to make preferred novel 4-oxocyclic urea compounds described herein.

4-Oxocyclic Urea Pharmaceutical Compositions Containing Novel 4-Oxocyclic Urea Compounds The novel 4-oxocyclic urea compounds of the present invention may be administered to humans or other mammals by a variety of routes, including, but not limited to, oral dosage forms and injections (intravenous, intramuscular, intraperitoneal and subcutaneous). Numerous other dosage forms containing the novel 4-oxocyclic urea compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the 4-oxocyclic urea compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular 4-oxocyclic urea compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

In particular, the solubility, acidity, and susceptibility to hydrolysis of the different 4-oxocyclic urea active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically-acceptable excipients include, but are not limited to, resins, fillers, binders, lubricants, solvents, glidants, disintegrants cosolvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Accordingly, the pharmaceutical compositions of the present invention include from 15–95% of a 4-oxocyclic urea compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein in Examples M–Q. It is well within the capabilities of one skilled in the art to vary the non-limiting examples described herein to achieve a broad range of pharmaceutical compositions.

Method Of Treating Arrhythmias With The Novel 4-Oxocyclic Urea Compounds

The novel compounds of the present invention are efficacious in treating humans or other mammals afflicted with supraventricular arrhythmias and ventricular arrhythmias, and/or cardiac fibrillation. As stated hereinabove, except in rare cases, supraventricular arrhythmias are not deemed to be life threatening and are generally not aggressively treated with conventional antiarrhythmic drugs due to their undesirable side effects. Accordingly, this type of arrhythmia is usually not aggressively treated to merely relieve symptoms which are characterized as mild to severe. However, the novel compounds of the present invention are generally well tolerated and generally exhibit less of the undesirable side effects than do may of the more conventional antiarrhythmic drugs and, accordingly, may well be an acceptable therapy to alleviate the symptoms suffered by individuals exhibiting supraventricular arrhythmias who are, in fact, experiencing discomfort, even though not in a life-threatening situation.

As stated hereinabove, the novel 4-oxocyclic urea compounds of the present invention are also effective in treating ventricular arrhythmias, which are, as a rule, much more serious than supraventricular arrhythmias and, accordingly, require aggressive therapy. Because of the potential seriousness of some ventricular arrhythmias, many patient-type classifications have arisen.

Individuals suffering from benign ventricular arrhythmias are, from a philosophical standpoint of whether-to-treat, similar to those individuals experiencing supraventricular arrhythmias. These individuals do not have heart disease and may experience dizziness, and palpitations, and often suffer from a certain amount of emotional distress stemming from uncertainty caused by their physical symptoms. These individuals generally suffer from PVCs which are, for the most part, physically harmless, but understandably give rise to some degree of anxiety. The novel 4-oxocyclic urea compounds of the present invention generally exhibit less of the undesirable side effects which may have made the use of many conventional antiarrhythmic drugs, heretofore reserved for more serious and/or life-threatening disease states, undesirable in these individuals. However, these individuals would likely benefit from therapy which is generally better-tolerated.

Another class of individuals who may benefit from therapy utilizing the novel 4-oxocyclic urea compounds of the present invention are those individuals who are characterized as having "prognostically significant" arrhythmias. These individuals generally have suffered a myocardial infarction and may have PVCs and/or episodes of non-sustained ventricular tachyarrhythmia, either symptomatic and asymptomatic. They do not exhibit the same degree of immediate, urgent life-threatening symptoms as do the those individuals described hereinbelow, and are not, by conventional characterization, in danger of immediate- or near-death. They are, however, at a significantly greater risk of cardiac failure than the general populace, and, accordingly, would be at a lessened risk of sudden death with therapy from the novel compounds of the present invention. See *Morganroth & Bigger* at 1498.

Other individuals exist who continually exhibit life-threatening arrhythmias and are in danger of immediate-or near-death. In these individuals, there is generally exhibited sustained ventricular tachyarrhythmia or ventricular fibrillation. The ventricular arrhythmias in these individuals generally produce hemodynamically significant signs or symptoms such as syncope, heart failure, myocardial ischemia or hypotension. These patients have the highest risk of sudden cardiac death and usually the most severe form of underlying cardiac disease. See *Morganroth and Bigger* at p. 1498. The novel compounds of the present invention are effective, aggressive antiarrhythmic therapy suitable for use in this class of individuals, but with less of some of the undesirable side effects generally heretofore tolerated with conventional antiarrhythmics, out of necessity and the unavailability of a suitable alternative to treat the life-threatening arrhythmias.

As stated above, the novel antiarrhythmic agents of the present invention exhibit less of many of the undesirable side effects associated with many conventional antiarrhythmic therapies. These side effects include, but are not limited to, period of the heart during each heartbeat. Conventional therapies exhibit anesthetic and/or cardiac depressive properties which merely make the heart less responsive, not less fibrillatory.

Accordingly, the novel 4-oxocyclic urea compounds of the present invention are useful in treating cardiac arrhythmias and/or cardiac fibrillation in humans or other mammals. Therefore, the present invention relates to a method for treating a human or other mammal suffering from cardiac arrhythmia and/or cardiac fibrillation which comprises administering to said human or other mammal a safe and effective amount of a pharmaceutical composition comprising from 15–90% of a 4-oxocyclic urea compound active ingredient or mixtures thereof, and from 10–85% pharmaceutically-acceptable excipients.

The Examples S–Z herein exhibit certain patient situations and illustrate the methods in which pharmaceutical compositions containing the novel 4-oxocyclic urea compounds of the prevent invention may be used to treat cardiac arrhythmias and fibrillation. It is well within the capabilities of one skilled in the art to vary the non-limiting examples described herein to treat a broad class of individuals suffering from cardiac arrhythmia and fibrillation.

The following examples will serve to further illustrate the present invention.

EXAMPLE A

Synthesis of 1-[[[5-(4-Chlorophenyl)-2-furanyl]methylene]amino]-3-[4-(4-methyl-1-piperazinyl)butyl]-2,4 -imidazolidinedione Dihydrochloride

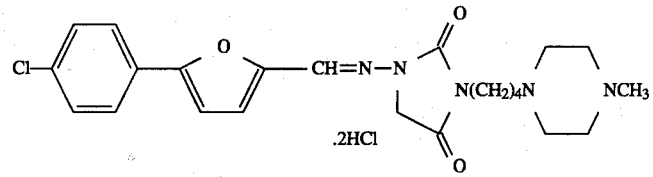

The above compound is prepared and synthesized as described hereinbelow.

I. Synthesis of 1-Phenylmethyleneamino-3-(4-chlorobutyl)-2,4 imidazolidinedione Dihydrochloride 1-Phenylmethylenamino-3-(4-chlorobutyl)-2,4-imidazolidinedione dihydrochloride is prepared by adding 60% sodium hydride in mineral oil (7.8 g, 0.1944 mole) over 1 hour to a stirred solution of 1-(benzylideneamino)hydantoin [prepared as described by J. Gut, A Novacet, and P. Fiedler, *Coll. Czech. Chem. Commun.*, Vol. 33, pp. 2087–2096 (No. 7). 1968 hereby incorporated by reference herein] (39.5 g, 0.1944 mole) in dimethylformamide (1000 ml). After complete addition, the solution is heated at steam bath temperature (approximately 100° C.) for 1.5 hours. The resulting mixture is allowed to cool to ambient temperature (30° C.). While stirring at ambient temperature, 1-bromo-4-chlorobutane (100 g, 0.5832 mole, 3 eq) is added in one portion. The mixture becomes exothermic reaching around 35° C. in approximately 30 minutes. The near-solution is heated at approximately 80° C. by steam bath for four hours, cooled and stirred for approximately eight hours at ambient temperature (30° C.). The cloudy mixture is filtered, removing a small amount of insoluble solid. The filtrate is concentrated under reduced pressure to a semi-solid residue. This residue is triturated with H$_2$O (400 ml), collected, recrystallized from acetonitrile, and then air-dried to give 43.1 g (0.1467 mole) of 1-phenylmethyleneamino-3-(4-chlorobutyl)-2,4-imidazolidinedione.

II. Synthesis of 1-Phenylmethyleneamino-3-(4-iodobutyl)-2,4-imidazolidinedione

A mixture of 1-phenylmethyleneamino-3-(4-chlorobutyl)-2,4 imidazolidinedione (prepared as described in Part I above) (43.1 g, 0.1467 mole), acetone (1200 ml) and sodium iodide (48.4 g, 0.3227 mole) is heated to reflux. Reflux is maintained for 5 hours. The mixture is filtered, collecting the insoluble. The filtrate is recharged with sodium iodide (10 g) and reflux is resumed and is maintained for 15 hours. After cooling to ambient temperature, the mixture is filtered, removing the insoluble NaCl (total recovery, 9.5 g, 110%). The filtrate is poured into H$_2$O (2000 ml) while stirring. After stirring for 30 minutes, the solid is collected and air-dried to yield 51.5 g (0.1337 mole) of 1-phenylmethyleneamino-3-(4-iodobutyl)-2,4-imidazolidinedione.

III. Synthesis of 1-Phenylmethyleneamino-3-[4-(4-methyl-1-piperazinyl)butyl]-2,4-imidazolidinedione Dihydrochloride A solution of 1-phenylmethyleneamino-3-(4-iodobutyl) 2,4-imidazolidinedione (10.0 g, 0.0260 mole) (prepared as described in Part II above), dimethylformamide (150 mg) and 1-methylpiperazine (11.5 ml, 10.4 g, 0.1040 mole) is heated to reflux. Reflux is maintained for 3 hours. After cooling to approximately 40° C., the solution is concentrated under reduced pressure by rotary evaporator to an oily-solid residue. This residue is dissolved in H$_2$O (200 ml) then made basic with saturated NaHCO$_3$ (200 ml). The resulting mixture is stirred for approximately 2 hours. The solid is collected and air-dried, and is next dissolved in absolute ethanol (150 ml), next filtered, then made acidic to wet litmus with EtOH/HCl. After cooling several hours, the solid is collected and air-dried to give 8.04 g (0.0187 mole) of 1-phenylmethyleneamino-3-[4-(4-methyl-1 -piperazinyl-)butyl]-2,4-imidazolidinedione dihydrochloride.

IV. Synthesis of 1-Amino-3-[4-(4-methyl-1-piperazinyl)butyl]-2,4-imidazolidinedione Hydrochloride A mixture of 1-phenylmethyleneamino-3-[4-(4-methyl-1-piperazinyl)butyl]-2,4-imidazolidinedione dihydrochloride (8.04 g, 0.0187 mole), 2N HCl (125 ml) and 5% Pd/C:50% H$_2$O (1.5 g, is subjected to hydrogen on a Parr apparatus at 40 psi at ambient temperature. After 2 hours, the catalyst is removed by filtration. The filtrate is divided into two equal portions. Each is concentrated under reduced pressure on a rotary evaporator to an oily residue of 1-amino-3-[4-(4-methyl-1-piperazinyl)butyl]-2,4-imidazolidinedione hydrochloride.

V. 1-[[[5-(4-Chlorophenyl)-2-furanyl]methylene]amino]-3-[4 -(4-methyl-1-piperazinyl)butyl]-2,4-imidazolidinedione dihydrochloride A solution of 1-amino-3-[4-(4-methyl-1-piperazinyl)butyl]-2,4-imidazolidinedione, hydrochloride (0.0094 mole), dimethylformamide (75 ml) and 5-(4-chlorophenyl)-2-furancarbox aldehyde [prepared as described in U.S. Pat. No. 4,882,354, to Huang et al., assigned to Norwich Eaton Pharmaceuticals, Inc., issued Nov. 21, 1984; see Cols. 7 and 8 hereby incorporated by reference herein] (1.94 g, 0.0094 mole) is stirred at ambient temperature for 72 hours. The mixture is filtered, collecting the solid. Recrystallization from absolute ethanol/H$_2$O and air-drying gives 2.63 g (0.0050 mole) of 1-[[[5-(4-chlorophenyl)-2-furanyl]methylene]amino]3-[ 4-methyl-1-piperazinyl)butyl]-2,4-imidazolidinedione dihydrochloride.

EXAMPLE B

Synthesis or 1-[[[5-(4-Chlorophenyl)-2-furanyl]methylene]-amino]-3-[8-(4-methyl-1-piperazinyl)octyl]-2,4-imidazolidinedione Dihydrochloride

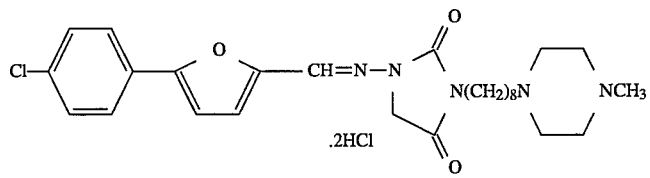

The above compound is prepared and synthesized as described hereinbelow.

I. Synthesis of 1-Benzylideneamino-3-(8-hydroxyoctyl)-2,4-imidazolidinedione 1-(Benzylideneamino)hydantoin is prepared according to the method set forth by J. Gut, A. Noracet, and P. Fiedler, *Coll. Czech. Chem. Commun.*, Vol. 33, pp. 2087–2096 (No. 7), 1968, hereby incorporated by reference herein.

To a solution of 30.5 g (0.15 mole) of 1-(benzylideneamino)hydantoin in 500 ml of dimethylformamide (DMF) is added in about 15 minutes with stirring, 6 g (0.15 mole) of sodium hydride (60% suspension in mineral oil). The temperature of the reaction mixture increases from 25° C. to 35° C. while a white solid separates in about 5 minutes after addition is completed. An additional 700 ml of dimethyl formamide is added to facilitate smooth stirring. The mixture is warmed to about 80° C. (steam bath) for 1 hour and is then allowed to cool. To this slightly cooled mixture at 50° C. is then added 24.7 g (0.15 mole) of 8-chloro-1-octanol. The mixture is then heated to 100°–110° C. for 3 hours and then allowed to cool for approximately 16 hours. A white solid disappears after the first hour of heating and then another solid gradually separates.

The resulting mixture is filtered and the filtrate is concentrated to about ⅓ of its original volume and is then poured into 1.2 liters of $H_2O$. The white precipitate is collected, washed well with water, and air-dried. The solid weighs 24 g (48%). Recrystallization of 3.5 g from 50 ml of nitromethane gives 2.86 g of 1-benzylideneamino-3-(8-hydroxyoctyl)-2,4-imidazolidinedione, as a crystalline white solid.

II. Synthesis of 1-Benzylideneamino-3-[8-(4-methyl-1-piperazinyl)octyl]-2,4-imidazolidinedione Dihydrochloride A mixture of 9.95 g (0.03 mole) of the above crude alcohol in 125 ml of benzene and 3.0 ml (0.04 mole) of thionyl chloride is heated at reflux for approximately 4 hours. The reaction mixture is filtered while hot and some insoluble material is collected. A small amount of solid separates from the filtrate upon cooling. The mixture is poured into about 400 ml of hexane and a white solid, octyl chloride, precipitates immediately. The precipitated octyl chloride is collected, washed well with hexane, and air-dried.

A mixture of 4.85 g (0.014 m) of the above precipitate and 1.5 g (0.015 mole) of N-methylpiperazine in 125 ml of dimethylformamide is heated at reflux. After 28 hours of heating at reflux, the mixture is concentrated at reduced pressure to give a brown residue. Trituration with saturated $NaHCO_3$ solution gives a brown solid. The mixture is filtered and the sticky brown solid collected is further triturated with ether and filtered again. This sticky solid is 1-benzylideneamino-3-[8 -(4-methyl-1-piperazinyl)octyl]-2,4-imidazolidinedione dihydrochloride (1.96 g).

III. Synthesis of 1-[[[5-(4-Chlorophenyl)-2-furanyl]methylene] amino]-3-[8-(4-methyl-1-piperazinyl)octyl]-2,4-imidazolidinedione Dihydrochloride A mixture of 1.96 g of the 1-benzylideneamino-3-[8 -(4-methyl-1-piperazinyl)octyl]-2,4-imidazolidinedione dihydrochloride in 100 ml of 2N HCl solution, together with 1.5 g of 5% palladium on carbon, is hydrogenated in a Parr shaker. Reduction ultimately takes 2 days, while another 1.5 g of palladium on carbon is added after 24 hours. Hydrogen uptake stops after 110% of theory and the catalyst is filtered off. The filtrate is concentrated at reduced pressure to give a dark solution with small amount of solid separating upon standing.

The above residue is diluted with 10 ml of dimethylformamide (DMF) and a solution of 0.98 g of 5-(4-chlorophenyl)-2-furancarboxaldehyde (prepared as described in U.S. Pat. No. 4,882,354, to Huang et al., assigned to Norwich Eaton Pharmaceuticals, Inc., issued Nov. 21, 1984; see Cols. 7 and 8 hereby incorporated by reference herein) in 10 ml of dimethylformamide is added. A yellowish solid separates almost immediately. After 4 hours of stirring, the mixture is filtered and the solid is washed thoroughly with SDA-32, and then ether and air-dried. Wt.=1.5 gm. Recrystallization of 2.27 g of this crude product from 350 ml of nitromethane gives 0.9 g of 1[[[5-(4-chlorophenyl)-2-furanyl]methylene] amino]-3-[8-(4 -methyl-1-piperazinyl]octyl]-2,4-imidazolidinedine dihydrochloride.

EXAMPLE C

Synthesis of 1-[[[5-(4-Chlorophenyl)-2-furanyl]methylene] amino]-3-[8-(4-morpholinyl)octyl]-2,4-imidazolidinedione Hydrochloride

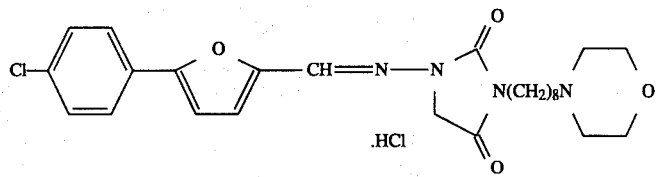

The above compound is prepared and synthesized as described hereinbelow.

A mixture of 5.0 g (0.015 mole) of the octyl chloride (synthesized in Part II of Example B) in 100 ml of dimethylformamide (DMF) and 1.5 g (0.017 mole) of morpholine is heated at reflux for 32 hours. The mixture is concentrated at reduced pressure to give a dark reddish residue. Trituration with saturated $NaHCO_3$ solution provides a brown solid which is collected, washed well with water, and then air-dried. This slightly sticky brown solid is dissolved in acetone, treated with activated charcoal, and filtered. The acetone filtrate is diluted with water until a solid starts to separate. The mixture is cooled and is then filtered. The solid is collected, washed well with water, and then air-dried to give 3.18 g (0.008 mole) of a sticky solid.

The above solid is placed in 100 ml of 2N HCl together with 1 g of 5% palladium on carbon catalyst and hydrogenated in a Parr shaker. Hydrogenation uptake stops after 6 hours (18 lb, 110%) and the mixture is filtered. The yellow filtrate is concentrated at reduced pressure on a rotary evaporator to give a brown, viscous liquid residue. To this liquid residue, in 10 ml of dimethylformamide, while stirring at ambient temperature, is added a solution of 1.65 g (0.008 mole) of 5-(4-chlorophenyl)-2-furancarboxaldehyde [prepared as described in U.S. Pat. No. 4,882,354, to Huang et al., assigned to Norwich Eaton Pharmaceuticals, Inc., issued Nov. 21, 1984; see Cols. 7 and 8 }hereby incorporated by reference herein) in 20 ml of dimethylformamide. The mixture is allowed to stir at ambient temperature for 16 hours and then concentrated at reduced pressure to give a brown residue. Fresh dimethylformamide is added to dissolve the solid and about 15 ml of ethanolic HCl solution is also added. The solution is heated at 40°–45° C. for 2 hours and then concentrated at reduced pressure. The resulting residue is triturated with absolute ethanol, and ethanol is removed at reduced pressure by rotary evaporator. This process is repeated once more and the brown semi-solid residue is triturated with ether and filtered. This sticky, mud-like solid is further triturated with isopropanol and filtered. The crude solid weighs 2.38 g and is recrystallized from SDA-32 to yield 1-[[[5-(4-chlorophenyl)-2-furanyl]methylene]amino]-3-[8 -(4-morpholinyl)octyl]-2,4-imidazolidinedione hydrochloride.

EXAMPLE D

Synthesis of 1-[[[3,5-Dimethyl-4-hydroxyphenyl]methylene]amino]-3-[4-(4-methyl-1-piperazinyl)butyl]-2,4-imidazolidinedione Dihydrochloride

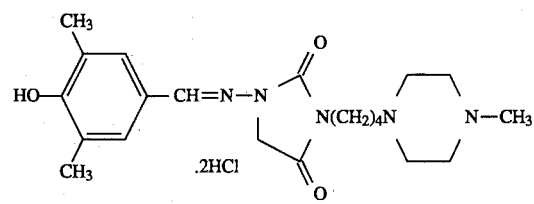

The above compound is prepared and synthesized as described hereinbelow.

A mixture of 3.23 g (0.0075 mole) of 1-phenylmethyleneamino-3-[4-(4-methyl-1-piperazinyl)butyl]-2,4-imidazolidinedone dihydrochloride (prepared as described in Parts I, II, and III of Example A) in 125 ml of 2N HCl, together with 2 g of 5% palladium on carbon (50% wet), is hydrogenated on a Parr shaker. Hydrogen uptake stops at 125% of theory. Catalyst is removed by filtration and the filtrate is concentrated at reduced pressure by rotary evaporator to give a sticky solid residue. This residue is repeatedly triturated with SDA-32 and the solvent is removed at reduced pressure on a rotary evaporator. A white solid is obtained.

The above solid is placed in 100 ml of dimethylformamide. After boiling for 10 minutes, no solution results. The mixture is cooled slightly and 1.13 g (0.0075 mole) of 3,5-dimethyl-4-hydroxybenzaldehyde is added. The mixture is allowed to stir overnight and is then warmed on a steam bath for 45 minutes. After cooling, the mixture is filtered and the solid is washed with dimethylformamide, SDA-32, ether and air-dried. The yield is 3.75 g (greater than 100%). Recrystallization from a mixture of 100 ml of SDA-32 and approximately 30 ml of $H_2O$ gives 2.17 g (66%) of 1-[[[3, 5-dimethyl-4-hydroxyphenyl]methylene]amino]-3-[ 4-(4-methyl-1-piperazinyl)butyl]-2,4-imidazolidinedione dihydrochloride.

EXAMPLE E

Synthesis of 1-[[[5-(4-Chlorophenyl)-2-furanyl]methylene] amino]-3-[3-[4-(2-hydroxyethyl)-1-piperazinyl]propyl]-2, 4-imidazolidinedione Dihydrochloride

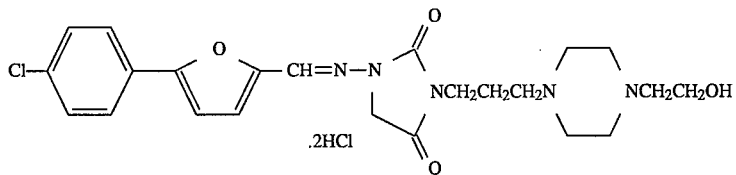

I. Synthesis of 1-[[[5-(4-Chlorophenyl)-2-furanyl]methylene] amino]-3-(3-chloropropyl)-2,4-imidazolididinedione A solution of 1-[5-(4-chlorophenyl)-2-furfurylideneamino]hydantoin [prepared as described in U.S. Pat. No. 3,415,821 by Davis and Snyder, assigned to Norwich Eaton Pharmaceuticals, Inc., issued Dec. 10, 1968; see Cols. 2 and 3, hereby incorporated by reference herein] (25.0 g, 0.082 mole) in AR grade dimethylformamide (423 ml) is stirred and swept with nitrogen. The solution is treated portion-wise with a mixture of sodium hydride (60%) in mineral oil [3.29 g, 0.082 mole) over a 5-minute period. The reaction mixture (later a solution followed by a thick mixture) is heated on a steam bath for 15 minutes. The reaction mixture is chilled to

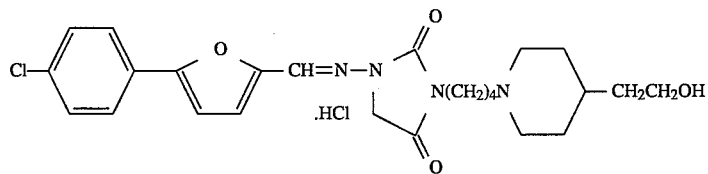

ambient temperature and the nitrogen sweep is then discontinued. The reaction is treated with 1-bromo-3-chloropropane (26.9 g, 0.165 mole) and heated on steam bath for 4 hours. The reaction mixture is chilled and poured over 1500 ml of water to leave an oily mixture. Upon standing for 5 minutes, a yellow solid is formed. The yellow solid is filtered and washed with water to give 1-[[[5-(4-chlorophenyl)-2-furanyl]methylene]amino]-3-(3 -chloropropyl)-2,4-imidazolidinedione (33.0 g).

II. Synthesis of 1-[[[5-(4-Chlorophenyl)-2-furanyl]methylene] amino]-3-[3-[4-(2-hydroxyethyl)-1-piperazinyl]propyl]-2,4-imidazolidinedione Dihydrochloride A stirred solution of 4-(2-hydroxyethyl)piperazine (3.83 g, 0.03 mole) in AR grade dimethylformamide (130 ml) is treated with 1-[[[5-(4-chlorophenyl)-2-furanyl]methylene] amino]-3-(3-chloropropyl)-2,4-imidazolidinedione (6.92 g, 0.015 mole). The reaction solution is heated at near reflux for 1.5 hours and then concentrated under reduced pressure to leave an oily residue. Said residue is treated with saturated sodium bicarbonate solution to give a yellow mixture. The mixture is filtered and washed with water to give 3.92 g crude product as the free base. The solid is dissolved in alcohol and treated with a mixture of saturated ethanolic/ HCl. The solution forms a crystalline solid after 5 minutes. The solid is collected by filtration to give the crude product. 1-[[[5-(4-Chlorophenyl)-2-furanyl]methylene]amino] -3-[3-[4-(2-hydroxyethyl)-1-piperazinyl]propyl]-2,4-imidazolidinedione dihydrochloride is isolated upon one recrystallization from 95% alcohol (2.57 g).

EXAMPLE F

Synthesis of 1-[[[5-(4-Chlorophenyl)-2-furanyl]methylene] amino]-3-[4-[4-(2-hydroxyethyl)piperidinyl]butyl]-2,4-imidazolidinedione Hydrochloride 1-[[[5-(4-Chlorophenyl)-2-furanyl]methylene]amino]-3-[ 4-(2-hydroxyethyl)piperidinyl]butyl]-2,4-imidazolidinedione hydrochloride is prepared and synthesized as described hereinbelow.

I. Synthesis of 1-[[[5-(4-Chlorophenyl-2-furanyl]methylene]amino]-3-(4-chlorobutyl)-2,4-imidazolidinedione.

To a stirred solution of 5-(4-chlorophenyl)-2-furancarboxaldehyde [prepared as described in U.S. Pat. No. 4,882, 354, to Huang et al., assigned to Norwich Eaton Pharmaceuticals, Inc., issued Nov. 21, 1984; see Cols. 7 and 8 (hereby incorporated by reference herein)] (26.0 g, 0.0856 mole) in dimethylformamide (500 ml) is added 60% NaH, in mineral oil (3.4 g, 0.0856 mole), portion-wise over 2 minutes. After addition, the mixture is stirred for 1 hour at ambient temperature, and then heated at steam bath temperature for 1 hour. The resulting thick mixture is cooled to ambient temperature. 1-bromo-3-chlorobutane (22.0 g, 0.1284 mole) is added and the mixture is stirred at ambient temperature for 30 minutes and then at 80°–90° C. for 2 hours. After cooling, the mixture is concentrated under reduced pressure to ⅓ of its volume. The reduced mixture is then poured into $H_2O$ (1500 ml) and is then stirred. The solid is collected, air-dried, and is then dried at 70° C. to give 35.5 g (0.090 mole, greater than 100% yield) of 1-[[[5-(4-chlorophenyl)-2-furanyl]methylene]amino]-3-(4-chlorobutyl)-2, 4-imidazolidinedione.

II. Synthesis of 1-[[[5-(4-Chlorophenyl)-2-furanyl]methylene] amino]-3-[4-[4-(2-hydroxyethyl)piperidinyl]butyl]-2, 4-imidazolidinedione Hydrochloride A stirred solution of 1-[[[5-(4-chlorophenyl)-2-furanyl] methlene]amino]-3-(4-chlorobutyl)-2,4-imidazolidinedione (5.0 g, 0.0127 mole), (prepared and described above), dimethylformamide (150 ml), sodium iodide (3.8 g, 0.0254 mole), $K_2CO_3$ (1.76 g, 0.0127 mole) and 4-piperidineethanol (4.1 g, 0.0318) is heated on a steam bath for 1.5 hour. After cooling, the mixture is concentrated under reduced pressure to a semi-solid residue. This residue is suspended in H₂O (300 ml) and is then extracted with CH₂Cl₂. The extract is washed with H₂O (3×100 ml) then dried over MgSO₄ (activated charcoal). The filtered solution is concentrated under reduced pressure to a solid residue. This is triturated with anhydrous ether, collected, and air-dried. This solid is dissolved in absolute EtOH (300 ml) with warming, cooled and made acidic with EtOH/HCl. After cooling on ice

EXAMPLE I

Synthesis of 1-[[[5-(4-Chlorophenyl)-2-furanyl] -methylene]amino]-3-[4-(4-methyl-1-piperazinyl)butyl]-2,4-imidazolidinedione Di-2-Z-butenedioic acid salt

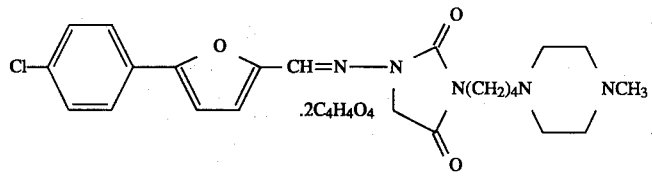

several hours, the solid is collected, washed with anhydrous ether, air-dried and dried at 70° to give 4.05 g (0.077 mole) of (4-chlorophenyl)-2-furanyl]methylene]amino]-3-[4-[4-(2-hydroxyethyl)piperidinyl]butyl]-2,4-imidazolidinedione hydrochloride.

EXAMPLE G

Synthesis of 1-[[[5-(4-Chlorophenyl)-2-furanyl]methylene]amino-3-[4-(4-methyl-1-piperazinyl)butyl]-2,4-imidazolidinedione

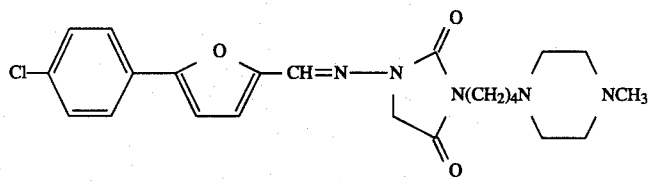

1-[[[5-(4-Chlorophenyl)-2-furanyl]methylene]amino-3-[4-(4-methyl-1-piperazinyl)butyl]-2,4-imidazolidinedine, a free-base, is prepared as described hereinbelow. The dihydrochloride salt, 1-[[[5-(4-Chlorophenyl)-2-furanyl]methylene]amino]-3-[4-(4-methyl-1-piperazinyl)butyl]-2,4 imidazolidinedione dihydrochloride, (6.56 g, 0.0124 mole) prepared as described in Example A herein, is dissolved in H₂O (300 ml) and washed with (1×100 ml). The aqueous phase is made basic with saturated NaHO₃ solution. The resulting mixture is extracted with CH₂Cl₂ (4×100 ml). The extract is washed with saturated NaCl (2×50 ml), dried over MgSO₄ (activated charcoal), filtered and concentrated under reduced pressure to a solid residue. This solid is triturated in anhydrous ether, collected and air-dried. Recrystallization once from absolute EtOH and then from toluene (activated charcoal), next washing with anhydrous ether and air drying gives 2.05 g (0.0045 mole) of 1-[[[5-(4-chlorophenyl)-2-furanyl]methylene]amino]-3-[4 -(4-methyl-1-piperazinyl)butyl]-2,4-imidazolidinedione.

EXAMPLE H

Any of the novel 4-oxocyclic urea hydrochloride salt compounds prepared in Examples A–F herein can be converted to their free-base form by utilizing the procedure set forth in Example G.

The di-2-Z-butenedioic acid salt of 1-[[[5-(4 -chlorophenyl)-2-furanyl]methylene]amino]-3-[4-(4-methyl-1-piperazinyl)butyl] -2,4-imidazolidinedione, is prepared as described hereinbelow.

The free base compound, 1-[[[5-(4-chlorophenyl)-2-furanyl]methylene]amino]-3-[4-(4-methyl-1-piperazinyl)butyl]-2,4-imidazolidinedione [prepared as described in Example G herein], (4.4 g, 0.0096 mole) is dissolved in MeOH (125 ml), treated with activated charcoal, and filtered. To this solution is added a solution of maleic acid (2.23 g, 0.0192 mole) in one portion. The resulting mixture is stirred at room temperature for approximately 2 hours and is then collected, and air-dried. This solid is recrystallized from absolute EtOH/H2O (activated charcoal), filtered then cooled. The solid is collected, washed with anhydrous ether, air-dried and dried at 70° C. to give 4.99 g (0.0072 mole) of 1-[[[5-(4-chlorophenyl)-2-furanyl]methylene]amino]-3-[4-(4-methyl-1-piperazinyl)butyl]-2,4-imidazolidinedione di-2-Z-butenedioic acid salt.

EXAMPLE J

Any of the compounds 4-oxocyclic urea hydrochloride salt synthesized herein in Example A–F and converted to their free base as described in Example H herein may be converted to their di-2-Z-butenedioic acid salt form by utilizing the procedure set forth in Example I.

EXAMPLE K

Synthesis of 1-[[[5-(4-Chlorophenyl)-2-furanyl]methylene]amino]-3-[3-[4-(2-hydroxyethyl)-1-piperazinyl]propyl]-2,4-imidazolidinedione

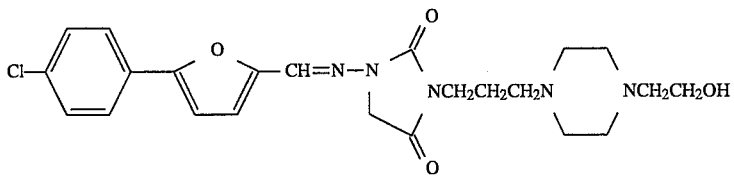

1-[[[5-(4-Chlorophenyl)-2-furanyl]methylene]amino]-3-[3-[4-(2-hydroxyethyl)-1-piperazinyl]propyl]-2,4-imidazolidinedione is prepared and synthesized as described hereinbelow.

1-[[[5-(4-Chlorophenyl)-2-furanyl]methylene]amino]-3-[3-[ 4-(2-hydroxyethyl)-1-piperazinyl]propyl-2,4-imidazolidinedione dihydrochloride, prepared as described in Example E, is dissolved in water (300 ml), followed by the addition of a solution of saturated sodium bicarbonate. A white solid precipitate is collected by filtration and washed with water to give 5.21 g of 1-[[[5-(4-chlorophenyl)-2-furanyl]methylene]amino]-3-[3-[ 4-(2-hydroxyethyl)-1-piperazinyl]propyl]-2,4-imidazolidinedione, the free base form of the 4-oxocyclic urea hydrochloride salt compound synthesized in Example E.

EXAMPLE L

Any of the compounds synthesized in Examples A–F can be converted to the free base form utilizing the procedure set forth in Example K.

EXAMPLE M

Preparation of 1-[[[5-(4-Chlorophenyl)-2-furanyl] methylene]amino]-3-[4-(4-methyl-1-piperazinyl)butyl]-2,4-imidazolidinedione Dihydrochloride oral tablet A tablet containing the compound, 1-[[[5-(4-chlorophenyl)-2-furanyl]methylene]amino]-3-[4-(4-methyl-1-piperazinyl)butyl]-2,4-imidazolidinedione dihydrochloride, prepared as described in Example A herein, has the following composition:

| ACTIVE INGREDIENT | |
|---|---|
| 1-[[[5-(4-Chlorophenyl)-2-furanyl]methylene]amino]-3-[4-(4-methyl-1-piperazinyl)butyl]-2,4-imidazolidinedione dihydrochloride | 350 mg |
| EXCIPIENTS | |
| Lactose | 192 mg |
| Sodium Starch Glycolate | 50 mg |
| Pregelatinized Starch | 30 mg |
| Talc | 12 mg |
| Magnesium Stearate | 6 mg |

Ten thousand tablets having the above composition are prepared as described below:

3.50 kg of 1-[[[5-(4-chlorophenyl)-2-furanyl]methylene]amino]-3-[4-(4-methyl-1-piperazinyl)butyl]-2,4-imidazolidinedione dihydrochloride, 1.92 kg of lactose, 0.50 kg of sodium starch glycolate, and 0.30 kg of pregelatinized starch are blended in the Patterson-Kelly blender and then granulated with water using the intensifier bar.

The granulation is next dried on trays in an oven or in a fluid bed dryer.

The granulation is milled through a 12-mesh screen using an oscillator or other suitable mill.

The granulation is blended with 120 g of talc and 60 g of magnesium stearate.

The talc magnesium and granulation mixture is compressed into 640 mg tablets on a suitable tablet machine.

The tablets prepared as described above are given to an individual suffering from cardiac arrhythmia and/or cardiac fibrillation utilizing a dosage regimen suitable for a particular patient.

EXAMPLE N

Preparation of 1-[[[5-(4-Chlorophenyl)-2-furanyl]methylene] amino]-3-[3-[4-(2-hydroxyethyl)-1-piperazinyl]propyl]-2,4-imidazolidinedione Dihydrochloride Oral tablet An oral tablet containing 1-[[[5-(4-chlorophenyl)-2-furanylmethylene]amino]-3-[3-[4-(2-hydroxyethyl)-1-piperazinyl]propyl]-2,4-imidazolidinedione dihydrochloride, prepared as described in Example E herein, have the following composition:

| ACTIVE INGREDIENT | |
|---|---|
| 1-[[[5-(4-Chlorophenyl)-2-furanylmethylene]amino]-3-[3-[4-(2-hydroxyethyl)-1-piperazinyl] propyl]-2,4-imidazolidinedione dihydrochloride | 300 mg |
| EXCIPIENTS | |
| Dibasic Calcium Phosphate | 219 mg |
| Crospovidone | 60 mg |
| Povidone | 12 mg |
| Talc | 6 mg |
| Magnesium Stearate | 3 mg |

Ten thousand tablets having the above composition are prepared as described below:

3.00 kg of 1-[[[5-(4-chlorophenyl)-2-furanyl]methylene]amino]-3[3-[4-(2-hydroxyethyl)-1-piperazinyl]propyl]-2,4-imidazolidinedione dihydrochloride, 2.19 kg of dibasic calcium phosphate, 0.60 kg of crospovidone, and 0.12 kg of povidone are blended in a Patterson-Kelly blender and then granulated with water using the intensifier bar.

The granulation is dried on trays in an oven or in a fluid bed dryer. The granulation is next milled through a 12-mesh screen using an oscillator or other suitable mill.

The granulation is blended with 60 g of talc and 30 g of magnesium stearate. Finally, the granulation, talc, and magnesium stearate mixture is compressed into 600 mg tablets on a suitable tablet machine.

Tablets prepared as described hereinabove are given to a patient suffering from cardiac arrhythmia and/or cardiac fibrillation, utilizing a dosage regimen suitable for the particular patient.

EXAMPLE O

Preparation of 1-[[[5-(4-Chlorophenyl)-2-furanyl] methylene]amino]-3-[4-(4-methyl-1-piperazinyl)butyl]-2,4-imidazolidinedione Dihydrochloride oral capsule An oral capsule containing 1-[[[5-(4-chlorophenyl)-2-furanyl]methylene]amino]-3-[4-(4-methyl-1-piperazinyl-)butyl]-2,4-imidazolidinedione dihydrochloride, prepared as described in Example A herein, has the following composition:

| ACTIVE INGREDIENT | |
| --- | --- |
| 1-[[[5-(4-Chlorophenyl)-2-furanyl]methylene]amino]-3-[4-(4-methyl-1-piperazinyl)butyl]-2,4-imidazolidinedione dihydrochloride | 300 mg |
| EXCIPIENTS | |
| Lactose | 92 mg |
| Sodium Starch Glycolate | 40 mg |
| Pregelatinized Starch | 25 mg |
| Talc | 12 mg |
| Magnesium Stearate | 3 mg |
| Hard Gelatin Capsule Shell | 1 per capsule |

Ten thousand oral capsules having the above composition are prepared as described below:

3.00 kg of 1-[[[5-(4-chlorophenyl)-2-furanyl]methylene]amino]-3-[4-(4-methyl-1-piperazinyl)butyl]-2,4-imidazolidinedione dihydrochloride, 0.92 kg of lactose, 0.40 kg of sodium starch glycolate, and 0.25 kg of pregelatinized starches are blended in a Patterson-Kelly blender and granulated with water using the intensified bar.

The granulation is dried on trays in an oven or in a fluid bed dryer.

The granulation is milled through a 12-mesh screen using an oscillator or other suitable mill. The granulation is blended with 120 g of talc and 30 g of magnesium stearate.

Finally, 472 mg of granulation, talc, and magnesium stearate mixture is filled into each capsule shell on a suitable capsule filling machine.

The capsule prepared as described above is given to a patient suffering from cardiac arrhythmia and/or cardiac fibrillation, in a suitable dosage regimen.

EXAMPLE P

Preparation of 1-[[[5-(4-Chlorophenyl-2-furanyl]methylene] amino]-3-[3-[4-(2-hydroxyethyl)-1-piperazinyl]propyl]-2,4-imidazolidinedione Dihydrochloride oral tablet An oral capsule containing 1-[[[5-[4-(chlorophenyl)-2-furanyl] methylene]amino]-3-[3-[4-(2-hydroxymethyl)-1-piperazinyl]propyl]-2,4-imidazolidinedione dihydrochloride prepared as described in Example E herein, has the following composition:

| ACTIVE INGREDIENT | |
| --- | --- |
| 1-[[[5-[4-(Chlorophenyl)-2-furanyl]methylene]amino]-3-[3-[4-(2-hydroxyethyl-1-piperazinyl]propyl]2,4-imidazolidinedione dihydrochloride | 175 mg |
| EXCIPIENTS | |
| Microcrystalline Cellulose | 120 mg |
| Crospovidone | 25 mg |
| Povidone | 5 mg |
| Talc | 5 mg |
| Magnesium Stearate | 2 mg |
| Hard Gelatin Capsule Shell | 1 per capsule |

Ten thousand capsules having the above composition are prepared as described below:

1.75 kg of 1-[[[5-[4-(chlorophenyl)-2-furanyl]methylene] amino] -3-[3-[4-(2-hydroxymethyl-1-piperazinyl]propyl]-2, 4-imidazolidindion dihydrochloride, 1.20 kg of microcrystalline cellulose, 0.25 kg of crospovidone, and 0.05 kg of povidone are blended in a Patterson-Kelly or other suitable blender and then granulated with water using the intensifier bar.

The granulation is dried on trays in an oven or a fluid bed dryer. The granulation is milled through a 12 mesh screen using an oscillator or other suitable mill. The granulation is blended with 50 g of talc and 20 g of magnesium stearate.

322 mg of the granulation, talc, and magnesium stearate mixture is filled into each capsule shell on a suitable capsule filling machine.

Capsules prepared as described above are given to patients suffering from cardiac arrhythmia and/or cardiac fibrillation, utilizing a suitable dosage regimen.

EXAMPLE Q

Preparation of 1-[[[5-(4-Chlorophenyl)-2-furanyl] methylene]amino]-3-[4-(4-methyl-1-piperazinyl)butyl]-2,4-imidazolidinedione Dihydrochloride
LYPHILIZED INJECTION A solution suitable for use as an intravenous (I.V.) injectioin has the following composition:

| ACTIVE INGREDIENT | |
| --- | --- |
| 1-[[[5-(4-Chlorophenyl)-2-furanyl]methylene]amino]-3-[4-(4-methyl-1-piperazinyl)butyl]-2,4-imidazolidinedione dihydrochloride | 400 mg |
| EXCIPIENTS | |
| Mannitol | 500 mg |
| Citric Acid/Sodium Citate | quantity sufficient to adjust pH to 5.5–6.5 |

The method to prepare 1,000 vials of the above solution for I.V. injection is described hereinbelow.

400 g of 1-[[[5-(4-Chlorophenyl)-2-furanyl]methylene] amino] -3-[4-(4-methyl-1-piperazinyl)butyl]-2,4-imidazolidinedione dihydrochloride, 500 g mannitol, and sufficient sodium citrate and/or citric acid to make a pH 5.5–6.5 solution are dissolved in 10.0 liters of sterile water for injection.

The resulting solution is aseptically filtered through a 0.2 micron filter and filled into vials in the amount of 10 ml per vial.

The vials are loaded into a lyophilizer, frozen, dried and stoppered. The lyophilized product is diluted with 10 ml of sterile water immediately prior to injection.

A patient suffering from cardiac arrhythmias and/or cardiac fibrillation is given an I.V. injection of the above solution, utilizing a suitable dosage regimen.

EXAMPLE R

Any 4-oxocyclic urea compound active ingredient prepared in any of Examples A–L can be substituted for the active ingredient utilized in the preparation of the various dosage forms of Examples M through Q.

EXAMPLE S

A 57-year-old white male is found unconscious and without palpable pulse at home. A family member initiates cardiopulmonary resuscitation. The first rhythm documented by the rescue squad is ventricular fibrillation. The patient is successfully resuscitated.

The patient had had a myocardial infarction three years ago, and has had stable angina since.

During the ensuing hospitalization, the patient is found not to have had a myocardial infarction. Monomorphic sustained ventricular tachyarrhythmia is induced by programmed electrical stimulation.

The patient's cardiologist prescribes 1-[[[5-(4-chlorophenyl)-2-furanyl]methylene]-amino]-3-[4-(4-methyl-1-piperazinyl)-butyl]-2,4-imidazolidinedione dihydrochloride at a dose of 350 mg twice a day, after meals. After four days of therapy, the arrhythmia is not inducible at a repeat programmed electrical stimulation study. The patient has no further episodes of cardiac arrest over the next 2 years, and treatment will continue.

EXAMPLE T

A 65-year-old black male has a syncopal spell preceded by sensations of palpitations. Over the preceding several months, the patient had experienced frequent palpitations, once with a near-fainting spell. He has a history of hypertensive cardiovascular disease, diabetes, remote myocardial infarction and obesity.

Sustained monomorphic ventricular tachycardia is induced by programmed electrical stimulation. The patient's cardiologist prescribes 1-[[[5-(4-chlorophenyl)-2-furanyl]methylene]-amino] -3-[4-(4-methyl-1-piperazinyl)butyl]-2,4-imidazolidinedione dihydrochloride at an oral dose of 350 mg once a day, after a meal. After several days of therapy, the arrhythmia is noninducible on repeat programmed electrical stimulation. There are no further episodes of syncope or presyncope over the next three years of observation.

EXAMPLE U

A 58-year-old female oriental patient with a cardiomyopathy presents with recurrent syncope. Her ejection fraction is 35%. Programmed electrical stimulation (PES) induces poorly tolerated sustained ventricular tachyarrhythmia unresponsive to three different antiarrhythmic drugs. A fourth drug, moricizine, reduces the rate of the tachyarrhythmia and is continued, but the tachyarrhythmia still induces hypotension. She undergoes implantation of an automatic implantable cardioverterdefibrillator (AICD).

The defibrillator discharges twice in the year after implantation of the AICD. The device's monitor records sustained ventricular tachyarrhythmia at the times of defibrillation. After the second discharge, the patient is hospitalized. Sustained monomorphic ventricular tachyarrhythmia is induced at PES. Moricizine is discontinued and 1-[[[5-(4-chlorophenyl)-2-furanyl]methylene]-amino]-3-[4-(4-methyl-1-piperazinyl)-butyl]-2,4-imidazolidinedione dihydrochloride at an oral dose of 350 mg twice a day, after meals, is started by the patient's cardiologist. At repeat PES several days later, the arrhythmia is not inducible and the defibrillation threshold is unchanged. Over the subsequent year of observation, no further discharges are experienced.

EXAMPLE V

A 35-year-old female presents with a 15-year history of frequent (2/month) spells of rapid heartbeat lasting several hours associated with dizziness and fatigue. These spells cause her to miss time from work. A transtelephonic event monitor demonstrates paroxysmal supraventricular tachycardia. The patient's physician prescribes 1-[[[5-(4-chlorophenyl)-2-furanyl]methylene]-amino]-3-[4-(2-hydroxyethyl)-1-piperazinyl]propyl]-2,4-imidazolidinedione dihydrochloride orally at a dose of 175 mg/day. Over the subsequent year of observation, the frequency of these spells decreases to one every other month, with marked improvement in her attendance record at work.

EXAMPLE W

A 75-year-old Caucasian male who has a fifty pack-year history of smoking has known episodes of atrial fibrillation documented by transtelephonic monitoring, at the rate of three per month while on therapy with digoxin and quinidine. These spells sometimes last over eight hours and prevent the patient's pursuit of his normal daily activities, such as gardening, due to weakness. The patient's physician switches the patient from quinidine to 1-[[[5-(4-chlorophenyl)-2-furanyl]methylene]amino]-3-[3-[4-(2-hydroxyethyl)-1-piperazinyl]propyl]-2,4-imidazolidinedione dihydrochloride orally at a dose of 175 mg/day. The frequency of spells decreases to one a month over the subsequent four months of observation.

EXAMPLE X

A 40-year-old Caucasian male has a several year history of frequent palpitations. The patient experiences anxiety and shortness of breath at the time of the palpitations, and has become preoccupied by a fear of death. Extensive evaluations have demonstrated an absence of structural heart disease. Holter monitoring has shown 2500 PVCs per day, unifocal, with 50 couplets per day. Neither reassurance, nor subsequent therapy with propranolol, have not been effective.

The physician prescribes 1-[[[5-(4-chlorophenyl)-2-furanyl]methylene]amino] -3-[4-(4-methyl-1-piperazinyl)butyl] -2,4-imidazolidinedione dihydrochloride at an oral dose of 350 mg/day, after a meal.

The frequency of the palpitations decreases and the associated anxiety and shortness of breath are relieved. Holter monitoring now shows 250 PVCs per day and no repetitive forms. The preoccupation with death resolves over several months. The patient is monitored closely, and continues to do well over the subsequent five years.

EXAMPLE Y

A fifty-eight-year old black male with a ten year history of non-insulin dependent diabetes mellitus and a cholesterol level exceeding 300 mg/dl has a myocardial infarction. Two weeks after the infarction, he is asymptomatic with the exception of dyspnea on exertion. His ejection fraction is 29%, and 24 hour. Holter monitoring reveals 50 unifocal PVCs per hour, occasional couplets, and one five beat run of ventricular tachyarrhythmia.

His cardiologist prescribes 1-[[[5-(4-chlorophenyl)-2-furanyl]methylene]amino]-3-[4-(4-methyl-1-piperazinyl)butyl]-2,4-imidazolidinedione dihydrochloride at an oral dose of 350 mg/day after meals. Repeat Holter monitoring shows abolition of all repetitive forms and an average of 9 PVCs per hour. The patient does well over the next three years of follow up.

EXAMPLE Z

Any of the patients described in Examples S–Y could be treated with any of the dosage forms synthesized in Examples M–Q, utilizing any of the above ingredients described in Examples A–L.

What is claimed is:

1. A novel 4-oxocyclic urea compound having the general structure:

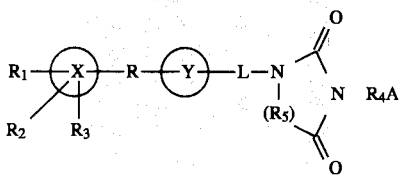

wherein a) X is a saturated or unsaturated, substituted or unsubstituted, 5-, 6-, or 7-membered heterocycle or 5-, 6-, 7-membered carbocycle; wherein, when X is a heterocycle, said heterocycle has one or two heteroatoms, independently selected from the group consisting of O and N; and wherein when heterocycle X or carbocycle X is substituted, said substituents are $R_1$, $R_2$, and $R_3$;

b) R is selected from the group consisting of covalent bond; nil; heteroatom; carboxyl; saturated or unsaturated, substituted or unsubstituted 5-, 6-, or 7-membered heterocycle having one or two heteroatoms, independently selected from the group consisting of O and N; saturated or unsaturated, substituted or unsubstituted 5-, 6-, or 7-membered carbocycle; alkyl; alkenyl; alkoxy; alkylamino; arylalkyl; aryloxy; acyl; acyloxy, and acylamino; wherein when said heterocycle or said carbocycle is substituted, said substitutents are selected from the group consisting of H, Cl, F, Br, $NH_2$, $CF_3$, OH, $SO_3H$, $CH_3SO_2NH$, COOH, alkoxy, alkoxycarbonyl, alkyl hydroxyalkyl, carboxyalkyl, aminoalkyl, acylamino, and acyloxy;

c) Y is a substituted or unsubstituted, saturated or unsaturated 5-, 6-, or 7-membered heterocycle having one or two heteroatoms, independently selected from the group consisting of O and N; a substituted or unsubstituted, saturated or unsaturated 5-, 6-, or 7-membered carbocycle; or is nil; wherein when said heterocycle or said carbocycle is substituted, said substitutents are selected from the group consisting of H, Cl, F, Br, $NH_2$, $CF_3$, OH, $SO_3H$, $CH_3SO_2NH$, COOH, alkoxy, alkoxycarbonyl, aminoalkyl, acylamino, and acyloxy;

and wherein when Y and R are nil, X is a carbocycle or heterocycle; and wherein when R is nil, X and Y are rings, independently selected from carbocycles and heterocycles, which are fused; and wherein when R is a covalent bond, X and Y are unfused rings, independently selected from carbocycles and heterocycles, linked together through covalent bond R; and wherein when Y is nil, R is a covalent bond and X is a carbocycle or heterocycle, then X is bound to L through R;

d) $R_1$, $R_2$, and $R_3$ are substituents on the X moiety and are independently selected from the group consisting of H, Cl, F, Br, $NH_2$, $CF_3$, OH, $SO_3H$, $CH_3SO_2NH$, COOH, alkoxy, alkoxycarbonyl, alkyl hydroxyalkyl, carboxyalkyl, aminoalkyl, acylamino, and acyloxy;

e) L is a linking moiety and is selected from the group consisting of alkylamino, alkenylamino, alkylimino, alkyenylimino, and acylamino; wherein the carbon-containing end of L is bound to the X-Y-R ring system at Y; but if Y is nil, through R, at X; and wherein the nitrogen atom of L is bound to the nitrogen atom at the 1-position of the 4-oxocyclic urea ring moiety;

f) $R_4$ is selected from the group consisting of an alkyl, alkenyl, alkynl, alkylacyl, and heteroalkyl;

g) A is a substituted or unsubstituted, saturated or unsaturated, straight-chain or branched $C_1$–$C_8$ alkylamino, wherein when said alkylamino is substituted, said substituents are selected from the group consisting of methyl, hydroxyethyl, alkyl, aryl, 5- or 6-membered heterocycle having one or two nitrogen atoms, phenylalkyl, mercaptoethyl, and methansulfonyl; or A is a substituted or unsubstituted, saturated or unsaturated heterocycle having 5-, 6-, or 7-members, and one or two heteroatoms independently selected from the group consisting of O and N; and wherein when heterocycle A is substituted, said substituents are selected from the group hydroxyethyl, alkyl, aryl, mercaptoethyl, methanesulfonyl, 5- or 6-membered heterocycle having one or two nitrogen atoms, and phenylalkyl, and A has one nitrogen atom which is adjacent to $R_4$; and wherein, when heterocycle A has six members and has one nitrogen atom and A is substituted, said substituents are hydroxyethyl, hydroxy oxo, and methyl; and h) $R^5$ is a substituted or unsubstituted $C_1$ or $C_2$alkyl.

2. A compound according to claim 1 wherein X is an unsaturated 6-membered carbocycle.

3. A compound according to claim 2 wherein X is unsubstituted and $R_1$, $R_2$, and $R_3$ are nil.

4. A compound according to claim 2 wherein is $R_1$, $R_2$, and $R_3$ are independently selected from the group consisting of nil, Cl, F, Br, $CH_3$, and OH.

5. A compound according to claim 2 wherein Y is a 5-, 6-, or 7-membered heterocycle.

6. A compound according to claim 5 wherein Y is a 5-membered heterocycle.

7. A compound according to claim 6 wherein R is a covalent bond.

8. A compound according to claim 2, wherein Y is a 5-membered heterocycle and wherein R is adjacent to X at the 1-position of X, and to Y at the 5-position of Y.

9. A compound according to claim 8 wherein Y is connected to the carbon-containing end of L at the 2-position of Y.

10. A compound according to claim 9 wherein a heteroatom of Y is oxygen at the 1-position of said heterocycle.

11. A compound according to claim 10 wherein one of $R_1$, $R_2$, or $R_3$ is Cl, F, or Br and two of $R_1$, $R_2$ or $R_3$ are nil.

12. A compound according to claim 1 selected from the group consisting of 1-[[[5-(4-chlorophenyl)-2-furanyl]methylene]amino]-3-[4-(4-methyl-1-piperazinyl)butyl]-2,4-imidazolidinedione; 1-[[[4-hydroxy-3,5-dimethylphenyl]methylene]amino]-3-[4-(4-methyl-1-piperazinyl)butyl]-2,4-imidazolidinedione; 1-[[[5-(4-chlorophenyl)-2-furanyl]

methylene]amino] -3-[3-[4-(1-methylethyl)-1-piperazinyl]propyl]-2,4-imidazolidinedione; 1-[[[5-(4-chlorophenyl)-2-furanyl]methylene]amino]-3-[3-[4 -(2-hydroxyethyl)-1-piperazinyl]propyl]-2,4-imidazolidinedione; 1-[[[5-(4-chlorophenyl)-2-furanyl]methylene]amino]-3-[6 -(4-methyl-1-piperazinyl)hexyl]-2,4-imidazolidinedione; 1-[[[5-(4-chlorophenyl)-2-furanyl]methylene]amino]-3-[5 -(4-methyl-1-piperazinyl)pentyl]-2,4-imidazolidinedione; 1-[[[5-(4-fluorophenyl)-2-furanyl]methylene]amino]-3-[4 -(4-methyl-1-piperazinyl)butyl]-2,4-imidazolidinedione; 1-[[[5-(4-chlorophenyl)-2-furanyl]methylene]amino]-3 -[4-[4-(2-hydroxyethyl)-1-piperidinyl]butyl]-2,4-imidazolidinedione; 1-[[[5-(4-chlorophenyl)-2-furanyl]methylene]-3-[3-[4-(2-hydroxyethyl)-1-piperidinyl]propyl]-2,4-imidazolidinedione; 1-[[[5-[4-chlorophenyl)-2-furanyl]methylene]amino]-3-[3-[4-(2-mercaptoethyl)-1-piperazinyl]propyl]-2,4-imidazolidinedione; 1-[[[5-(4-bromophenyl)-2-oxazolidinyl]methylene]amino]-3-[4-[4-methyl-1-piperazinyl)butyl]-2,4-imidazolidinedione; 1-[[[5-(4-chlorophenyl)-2-furanyl]methylene]amino]-3-[3-(dimethylaminopropyl]dihydro-2,4-(1H,3H)pyrimidinedione; 1-[[[5-(4-chlorophenyl)-2-furanyl]methylene]amino]-3-(3 -dimethylaminopropyl)-2,4-imidazolidinedione; 1-[[[5-(4-chlorophenyl)-2-furanyl]methylene]amino]-3-[3-(4-methyl-1 -piperazinyl)propyl]-2,4-imidazolidinedione; 1-[[[5-(4-fluorophenyl)-2-furanyl]methylene]amino]-3-[3-[4-(2 -hydroxyethyl)-1-piperazinyl]propyl]-2,4-imidazolidinedione; 1-[[[5-(4-chlorophenyl)-2-furanyl]methylene]amino]-3-[8 -(4-morpholinyl)octyl]-2,4-imidazolidinedione; and the pharmaceutically acceptable hydrochloride and maleate salts thereof.

13. A compound according to claim 1 wherein R is nil and X and Y are fused rings.

14. A compound according to claim 13 wherein X is a 6-membered carbocycle and Y is a 5-membered heterocycle.

15. A compound according to claim 1 where R is a heteroatom.

16. A compound according to claim 15 wherein R is oxygen.

17. A compound according to claim 1 wherein R is a covalent bond and Y is nil and X is a 6-membered carbocycle or heterocycle.

18. A compound according to claim 17 wherein X is a carbocycle.

19. A compound according to claim 17 wherein 18 is substituted with two or more substituents selected from the group consisting of Cl, OH, methoxy, methyl, and benzoyl.

20. A compound according to claim 1 wherein L is selected from the group consisting of alkylimino, alkylamino, and alkenylimino.

21. A compound according to claim 1 wherein $R_5$ is a $C_1$ alkyl.

22. A compound according to claim 1 wherein $R_4$ is $C_3$–$C_6$ alkyl.

23. A compound according to claim 1 wherein $R_4$ is a substituted alkyl.

24. A compound according to claim 1 wherein A is a heteroalkyl.

25. A compound according to claim 1 wherein the nitrogen atom of heteroalkyl A is substituted.

26. A compound according to claim 1 wherein A is a heterocycle.

27. A compound according to claim 26 wherein A has two nitrogen atoms.

28. A compound according to claim 27 wherein the nitrogen atom of A not connected to $R_4$ is substituted.

29. A compound according to claim 26 wherein heterocycle A has 6-members and is substituted at the 4-position.

30. A compound according to claims 25, or 28 wherein the substituents are selected from the groups consisting of methyl, hydroxyethyl, alkyl, aryl, heterocycle, arylalkyl, mercaptoethyl, and methanesulfonyl.

31. A compound according to claim 29 wherein said substituents are selected from the group consisting of hydroxyethyl, hydroxy, oxo, and methyl.

32. A pharmaceutical composition useful for the treatment of humans or other mammals afflicted with cardiac arrhythmias and/or cardiac fibrillation, said composition being comprised of a safe and effective amount of from 15 to 90% of a 4-oxocyclic urea compound of claim 1, or mixtures thereof, and from 10 to 85% pharmaceutically-acceptable excipients.

33. A pharmaceutical composition according to claim 32, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

34. A pharmaceutical composition according to claim 33 comprised of from 15–95% of the 4-oxocyclic urea active ingredient (or mixture thereof); 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

35. A method of treatment for humans or other mammals afflicted with cardiac arrhythmias and/or cardiac fibrillation comprised of administering to said human or other mammal a safe and effective amount of the pharmaceutical composition of claim 32.

* * * * *